(12) United States Patent
DeLuca et al.

(10) Patent No.: US 8,410,080 B1
(45) Date of Patent: Apr. 2, 2013

(54) 2-METHYLENE-VITAMIN D ANALOGS AND THEIR USES

(71) Applicant: Wisconsin Alumni Research Foundation, Madison, WI (US)

(72) Inventors: Hector F. DeLuca, Deerfield, WI (US); Lori A. Plum, Arena, WI (US); Rafal R. Sicinski, Warsaw (PL); Izabela Sibilska, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/649,240

(22) Filed: Oct. 11, 2012

Related U.S. Application Data

(60) Provisional application No. 61/550,172, filed on Oct. 21, 2011.

(51) Int. Cl.
*A61K 31/59* (2006.01)
*C07C 401/00* (2006.01)

(52) U.S. Cl. .................................... 514/167; 552/653

(58) Field of Classification Search .................. 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,843,928 A | 12/1998 | Deluca et al. | |
| 5,936,133 A | 8/1999 | Deluca et al. | |
| 5,945,410 A | 8/1999 | DeLuca et al. | |
| 6,392,071 B1 | 5/2002 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |

OTHER PUBLICATIONS

Sibilska et al., abstract of e-publication on Mar. 27, 2010 (Journal of Steroid Biochemistry and Molecular Biology, vol. 121(1-2) (Jul. 2010) 51-55).*

Osterm et al., "24- and 26-homo-1,25-dihyroxyvitamin D3: Preferential Activity in Inducing Differentiation of Human Leukemia Cells HL-60 in vitro", Proc. Natl. Acad. Sci. USA, 1987, 84: 2610-2614.

Perlman et al., "1alpha,25-dihyroxyvitamin D3, A Novel Vitamin D-related Compound with Potential Therapeutic Activity", Tetrahedron Letters, 1990, 31: 1823-1824.

Okano et al., "Regulatory Activites of 2beta-(3-Hydroxypropoxy)-1alpha,25-Dihydroxyvitamin D3, A Novel Synthetic Vitamin D3 Derivative, on Calcium Metabolism", Biochem. Biophys. Res. Commun., 1989, 163(3): 1444-1449.

Miyamoto et al., "Synthetic Studies of Vitamin D Analogs. XIV. Synthesis and Calcium Regulating Activity of Vitamin D3 Analogs Bearing a Hydroxyalkoxy Group at the 2beta-Position", Chem. Pharm. Bull., 1993, 41(6): 1111-1113.

(Continued)

*Primary Examiner* — Sabiha N Qazi
(74) *Attorney, Agent, or Firm* — Andrus, Sceales, Starke & Sawall, LLP

(57) ABSTRACT

This invention discloses 2-methylene-vitamin D analogs, and specifically (20S)-1α,25 -dihydroxy-2-methylene-vitamin $D_3$ as well as (5E)-(20S)-1α,25-dihydroxy-2 -methylene-vitamin $D_3$ and (20R)-1α,25-dihydroxy-2-methylene-vitamin $D_3$, as well as pharmaceutical uses therefor. These compounds exhibit relatively high binding activity and pronounced activity in arresting the proliferation of undifferentiated cells and inducing their differentiation to the monocyte thus evidencing use as an anti-cancer agent especially for the treatment or prevention of osteosarcoma, leukemia, colon cancer, breast cancer, skin cancer or prostate cancer. These compounds also have relatively high calcemic activities evidencing use in the treatment of bone diseases.

47 Claims, 15 Drawing Sheets

HL-60 Cell Differentiation $EC_{50}$: $1,25(OH)_2D_3 = 3 \times 10^{-9}$ M
2EG-S = $6 \times 10^{-11}$ M

OTHER PUBLICATIONS

Nishii et al., "The Development of Vitamin D3 Analogs for the Treatment of Osteoporosis", Osteoporosis International, 1993, 1: 190-193.

Inhoffen et al., "Studies in the Vitamin D Series,XXI: Hydrine Compounds from Bitamin D3", Chemische Berichte, 1957, 90: 664-673.

Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

Sicinski et al., "New Highly Calcemic 1alpha,25-dihydroxy-19-Norvitamin D3 Compounds with Modified Side Chain: 26,27-dihomo- and 26,27-dimethylene Analogs in 20S-Series", Steroids, 2002, 67: 247-256.

Grzywacz et al., "2-Methylene Analogs of 1alpha-hydroxy-19-norvitamin D3; Synthesis, Biological Activities of Docking to the Ligand Binding Domain of the Rat Vitamin D Receptor", J. Steroid Biochem, 2004, 89-90: 13-17.

Windaus et al., "The Constitution of Vitamin D2: Part II", Annalen der Chemie, 1936, 524: 295-299.

Posner et al., "Stereocontrolled Total Synthesis of Calcitrol Derivatives: 1,25-Dihyroxy-2-(4'-hydroxybutyl)vitamin D3 Analogs of an Osteoporosis Drug", Journal of Organic Chemistry, 1994, 59: 7855-7861.

Posner et al., "2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing", Journal of Organic Chemistry, 1995, 60: 4617-4626.

Perlman et al., "Novel Synthesis of 19-Nor-Vitamin D Compounds", Tetrahedron Letters, 1991, 32: 7663-7666.

Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.

Arbour et al., "A Highly Sensitive Method for Large-Scale Measurements of 1,25-Dihydroxyvitamin D", Analytical Biochemistry, 1998, 255: 148-154.

Collins et al., "Normal Functional Characteristics of Cultured Human Promyelocytioc Leukemia Cells (HL-60) After Induction of Differentiation by Dimethylsulfoxide", The Journal of Experimental Medicine, 1979, 149: 969-974.

Glebocka et al., "New 2-Alkylidene 1Alpha,25-Dihydroxy-19-norvitamin D3 Analogues of High Intestinal Activity: Synthesis and Biological Evaluation of 2-(3'-Alkoxypropylidene) and 2-(3'-Hydroxyproplidene) Derivatives", J. Med. Chem, 2006, 49: 2909-2920.

Arndt, "Diazomethane", Organic Synthesis, Coll., 1935, 15: 3.

Arndt, "Nitrosomethylurea", Organic Synthesis, Coll., 1935, 15: 48.

Barrack et al., "Potential Inhibitors of Vitamin D Metabolism: An Oxa Analogue of Vitamin D", Journal of Organic Chemistry, 1988, 53: 1790-1796.

Mascarenas et al., "Passadium-Catalysed Coupling of Vinyl Triflates with Enynes and its Application to the Synthesis of 1Alpha,25-Dihydroxyvitamin D3", Tetrahedron, 1991, 47(20:21): 3485-3498.

Sanches-Abella et al., "Synthesis and Biological Activity of Previtamin D3 Analogues with A-ring Modifications", Bioorganic & Medicinal Chemistry, 2008, 16: 10244-10250.

* cited by examiner

2-METHYLENE-VITAMIN D ANALOGS AND THEIR USES

BACKGROUND OF THE INVENTION

This invention relates to vitamin D compounds, and more particularly to 2-Methylene-Vitamin D analogs and their pharmaceutical uses, and especially (20S)-1α,25-dihydroxy-2-methylene-vitamin $D_3$, its biological activities, and its pharmaceutical uses, and (5E)-(20S)-1α,25-dihydroxy-2-methylene-vitamin $D_3$, its biological activities, and its pharmaceutical uses, as well as (20R)-1α,25-dihydroxy-2-methylene-vitamin $D_3$, its biological activities, and its pharmaceutical uses. This latter compound can also be named simply as 1α,25-dihydroxy-2-methylene-vitamin $D_3$ since the 20-methyl substituent is in its natural or "R" orientation.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. Nos. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

Analogs of the natural hormone 1α,25-dihydroxyvitamin $D_3$ characterized by the transposition of the A-ring exocyclic methylene group from carbon 10 (C-10) to carbon 2 (C-2) (e.g., 1α,25-dihydroxy-2-methylene-19-nor-vitamin D analogs) have been synthesized and tested [see Sicinski et al., J. Med. Chem., 41, 4662 (1998); Sicinski et al., Steroids 67, 247 (2002); and, DeLuca et al., U.S. Pat. Nos. 5,843,928; 5,936,133 and 6,382,071)]. Molecular mechanics studies performed on these analogs predict that a change of A-ring conformation may cause flattening of the cyclohexanediol ring. Molecular mechanics calculations and NMR studies also predict that the A-ring conformational equilibrium would be ca. 6:4 in favor of the conformer having an equatorial 1α-OH. It was further predicted that introduction of the 2-methylene group into 19-nor-vitamin D carbon skeleton would change the character of its 1α- and 3β-A-ring hydroxyls. They would both be in allylic positions similar to the 1α-hydroxyl group in the molecule of the natural hormone [i.e., 1α,25-$(OH)_2D_3$]. It was found that 1α,25-dihydroxy-2-methylene-19-nor-vitamin D analogs are characterized by significant biological potency. In addition, the biological potency of such analogs may be enhanced dramatically where "unnatural" (20S)-configuration is present. Taking into account these findings, the present invention is aimed at vitamin D compounds characterized by the presence of an additional A-ring exocyclic methylene group at carbon 2 (C-2) (e.g., 2-methylene-vitamin D analogs).

SUMMARY OF THE INVENTION

The present invention is directed toward 2-methylene-vitamin D analogs having methylene groups at the C-2 and C-10 positions on the A-ring, or at the C-2 and C-4 positions on the A-ring, and their pharmaceutical uses, and more specifically toward (20S)-1α,25-dihydroxy-2-methylene-vitamin $D_3$, its biological activity, and various pharmaceutical uses for this compound, and (5E)-(20S)-1α,25-dihydroxy-2-methylene-vitamin $D_3$, its biological activities, and its pharmaceutical uses, as well as (20R)-1α,25-hydroxy-2-methylene-vitamin $D_3$, its biological activities, and its pharmaceutical uses.

Structurally these 2-methylene-vitamin D analogs are characterized by the general formula I shown below:

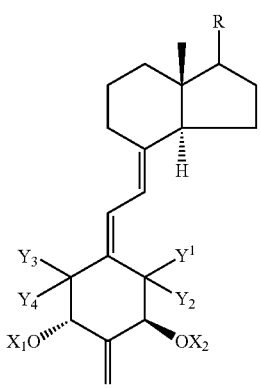

I where $X_1$ and $X_2$ are selected from the group consisting of hydrogen and a hydroxy-protecting group, where $Y_1$ and $Y_2$ are each hydrogen or taken together represent a methylene group, where $Y_3$ and $Y_4$ are each hydrogen or taken together represent a methylene group, with the provisos that when $Y_1$ and $Y_2$ are both hydrogen then $Y_3$ and $Y_4$ must be a methylene group, or when $Y_1$ and $Y_2$ taken together are a methylene group then $Y_3$ and $Y_4$ must both be hydrogen, or when $Y_3$ and $Y_4$ are both hydrogen then $Y_1$ and $Y_2$ must be a methylene group, or when $Y_3$ and $Y_4$ taken together are a methylene group then $Y_1$ and $Y_2$ must both be hydrogen, and where the group R represents any of the typical side chains known for vitamin D type compounds. Thus, R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

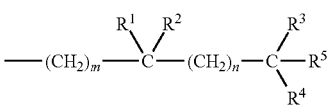

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =CR$^2$R$^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

Specific important examples of side chains are the structures represented by formulas (a), (b), (c), (d) and (e) below with natural 20R-configuration, i.e., the side chain as it occurs in 25-hydroxyvitamin D$_3$ (a); vitamin D$_3$ (b); 25-hydroxyvitamin D$_2$ (C); vitamin D$_2$ (d); and the C-24 epimer of 25-hydroxyvitamin D$_2$ (e).

Additional important examples of side chains are the structures represented by formulas (a), (b), (c), (d) and (e) below having the 20-epi or 20S-configuration, i.e., the side chain as it occurs in (20S)-25-hydroxyvitamin D$_3$ (a); (20S)-vitamin D$_3$ (b); (20S)-25-hydroxyvitamin D$_2$ (c); (20S)-vitamin D$_2$ (d); and the C-24 epimer of (20S)-25-hydroxyvitamin D$_2$ (e).

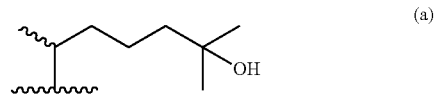

(a)

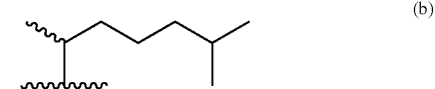

(b)

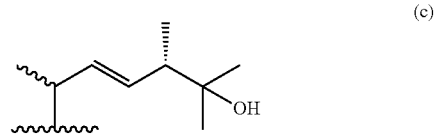

(c)

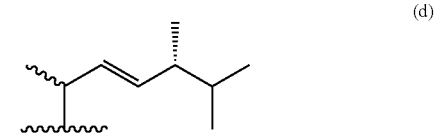

(d)

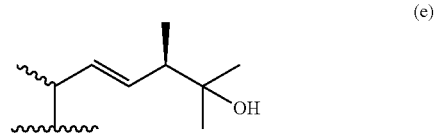

(e)

The wavy line to the carbon 20 indicates that carbon 20 may have either the R or S configuration.

The preferred analogs are (20S)-1α,25-dihydroxy-2-methylene-vitamin D$_3$ (which is referred to herein as "2EG-S") which has the following formula Ia:

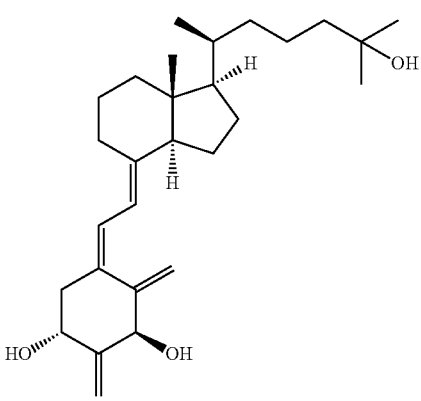

and (5E)-(20S)-1α,25-dihydroxy-2-methylene-vitamin D₃ (which is referred to herein as "T-2EG-S") which has the following formula Ib:

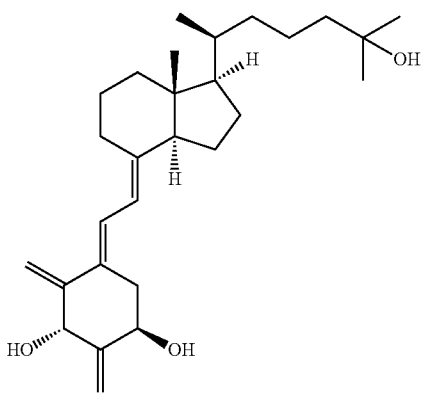 [SMILES: C=C1/C(=C/C=C2\CCC[C@]3(C)[C@@H]([C@@H](C)CCCC(C)(C)O)CC[C@@H]23)C[C@@H](O)C(=C)[C@@H]1O]

and (20R)-1α,25-dihydroxy-2-methylene-vitamin D₃ (which is referred to herein as "2EG-R") which has the following formula Ic:

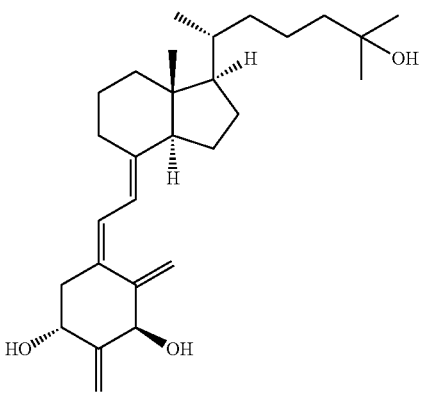

Compound Ic may also be named "2-methylene-1α,25-dihydroxy-vitamin D₃" herein.

The above compounds of formula I, especially formula Ia, Ib, and Ic exhibit a desired, and highly advantageous, pattern of biological activity. These compounds are characterized by relatively high binding to vitamin D receptors, i.e. they bind with about the same or only slightly lower affinity than 1α,25-dihydroxyvitamin D₃. They are all very potent in causing differentiation of HL-60 cells. They also exhibit relatively high transcriptional activity as well as relatively high activity in their ability to mobilize calcium from bone, and in their ability to promote intestinal calcium transport, as compared to 1α,25-dihydroxyvitamin D₃. Hence, these compounds can be characterized as having relatively high calcemic activity.

The above compounds I, and particularly Ia, Ib, and Ic, have relatively high binding affinity, are characterized by relatively high cell differentiation activity, and have relatively high calcemic activities. Thus, these compounds have potential as anti-cancer agents and provide therapeutic agents for the prevention or treatment of osteosarcoma, leukemia, colon cancer, breast cancer, skin cancer and prostate cancer. These analogs may also serve as important therapies for bone diseases like senile osteoporosis, postmenopausal osteoporosis, steroid-induced osteoporosis, low bone turnover osteoporosis, osteomalacia, and renal osteodystrophy.

One or more of the compounds may be present in a composition to treat or prevent the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of 2EG-S and 1,25(OH)₂D₃ to compete for binding with [³H]-1,25-(OH)₂-D₃ to the full-length recombinant rat vitamin D receptor;

FIG. 2 is a graph illustrating the percent HL-60 cell differentiation as a function of the concentration of 2EG-S and 1,25(OH)₂D₃;

FIG. 3 is a graph illustrating the in vitro transcription activity of 1,25(OH)₂D₃ as compared to 2EG-S;

FIG. 4 is a bar graph illustrating the bone calcium mobilization activity of 1,25(OH)₂D₃ as compared to 2EG-S; and FIG. 5 is a bar graph illustrating the intestinal calcium transport activity of 1,25(OH)₂D₃ as compared to 2EG-S.

FIG. 6 is a graph illustrating the relative activity of T-2EG-S and 1,25(OH)₂D₃ to compete for binding with [³H]-1,25-(OH)₂-D₃ to the full-length recombinant rat vitamin D receptor;

FIG. 7 is a graph illustrating the percent HL-60 cell differentiation as a function of the concentration of T-2EG-S and 1,25(OH)₂D₃;

FIG. 8 is a graph illustrating the in vitro transcription activity of 1,25(OH)₂D₃ as compared to T-2EG-S;

FIG. 9 is a bar graph illustrating the bone calcium mobilization activity of 1,25(OH)₂D₃ as compared to T-2EG-S; and FIG. 10 is a bar graph illustrating the intestinal calcium transport activity of 1,25(OH)₂D₃ as compared to T-2EG-S.

FIG. 11 is a graph illustrating the relative activity of 2EG-R and 1,25(OH)$_2$D$_3$ to compete for binding with [$^3$H]-1,25-(OH)$_2$-D$_3$ to the full-length recombinant rat vitamin D receptor;

FIG. 12 is a graph illustrating the percent HL-60 cell differentiation as a function of the concentration of 2EG-R and 1,25(OH)$_2$D$_3$;

FIG. 13 is a graph illustrating the in vitro transcription activity of 1,25(OH)$_2$D$_3$ as compared to 2EG-R;

FIG. 14 is a bar graph illustrating the bone calcium mobilization activity of 1,25(OH)$_2$D$_3$ as compared to 2EG-R; and FIG. 15 is a bar graph illustrating the intestinal calcium transport activity of 1,25(OH)$_2$D$_3$ as compared to 2EG-R.

DETAILED DESCRIPTION OF THE INVENTION

Figure 1:
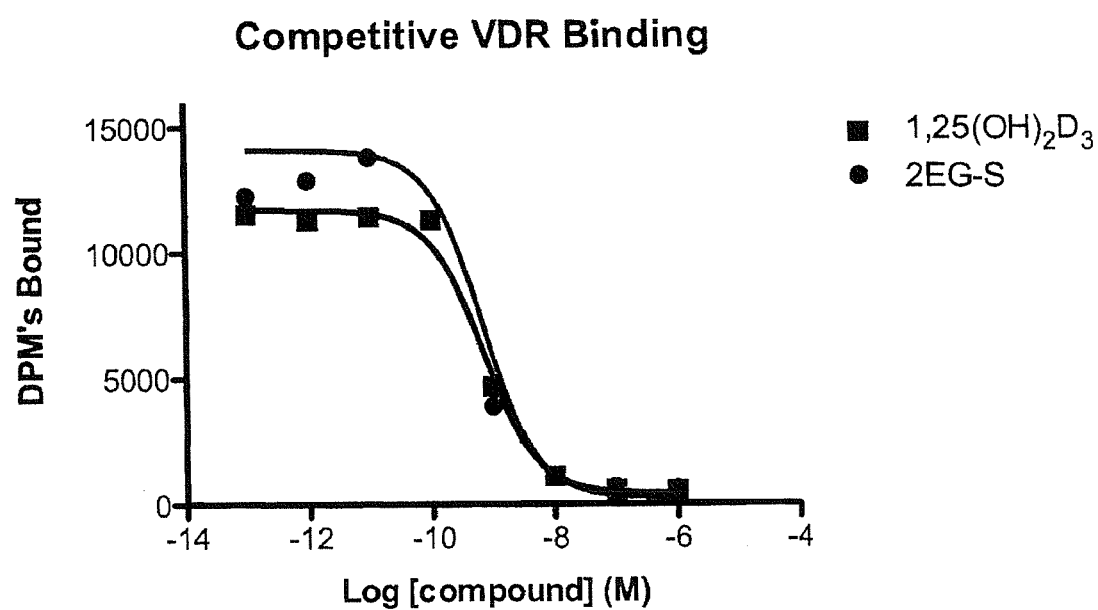
FIGS. 1-5 illustrate various biological activities of (20S)-1α,25-dihydroxy-2-methylene-vitamin D₃, hereinafter referred to as "2EG-S," as compared to the native hormone 1α,25-dihydroxyvitamin D₃, hereinafter "1,25(OH)₂D₃."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$-where k is an integer.

The preparation of 2-methylene-vitamin D analogs of the basic structure I can be accomplished by a common general method, i.e., a Sonogashira coupling of a bicyclic vinyl compound II with the dienyne III:

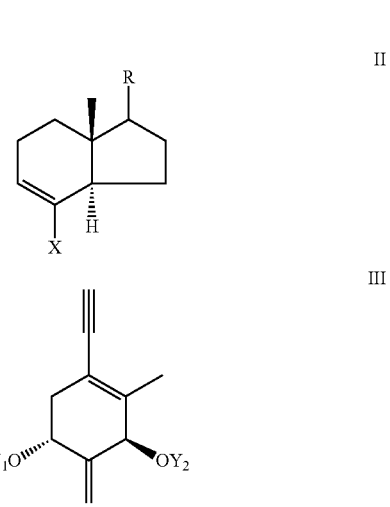

In the structures II and III, group X represents a leaving group selected from halogen (iodine, bromine or chlorine) and alkyl- or aryl-sulphonyloxy such as mesyloxy, tosyloxy or—most preferably—trifloxy. Groups $Y_1$, $Y_2$ and R represent groups defined above; $Y_1$ and $Y_2$ being preferably hydroxy-protecting group, it being also understood that any functionalities in R that might be sensitive, or that interfere with the coupling reaction, be suitable protected as is well-known in the art. The process shown above represents an application of the convergent synthesis concept, which has been applied effectively for the preparation of vitamin D compounds [Mascarenas et al., Tetrahedron 47, 3485 (1991), Barrack et al., J. Org. Chem., 53, 1790 (1988); Sanchez-Abella et al., Bioorg. Med. Chem. 16, 10244 (2008)].

Bicyclic compounds of the general structure II are known, or can be easily prepared by known methods from the corresponding Windaus-Grundmann type ketones. Specific important examples of such known bicyclic ketones are the structures with the side chains (h), (i), (j), (k), (l), (m), and (n) below described above, i.e., 25-hydroxy Grundmann's ketone (h) [Baggiolini et al., J. Org. Chem., 51, 3098 (1986)]; Grundmann's ketone (i) [Inhoffen et al., Chem. Ber., 90, 664 (1957)]; 25-hydroxy Windaus ketone (j) [Baggiolini et al., J. Org. Chem., 51, 3098 (1986)]; Windaus ketone (k) [Windaus et al., Ann., 524, 297 (1936)]; (20S)-25-hydroxy Grundmann's ketone (l) [Sicinski et al., J. Med. Chem., 41, 4662 (1998)]; (20S)-Grundmann's ketone (m) [Grzywacz et al., J. Steroid Biochem. Mol. Biol., 89-90, 13 (2004)]; and (20S)-25-methyl Grundmann's ketone (n) [Grzywacz et al., J. Steroid Biochem. Mol. Biol., 89-90, 13 (2004)]:

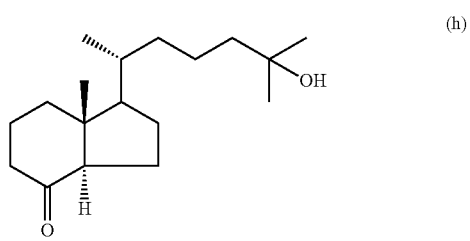

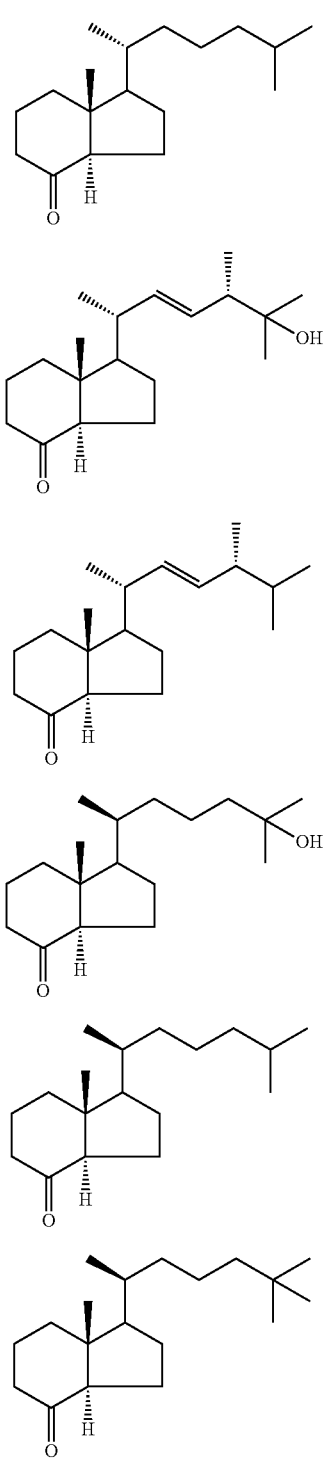

as silyl ether. The dehydration of the tertiary hydroxyl compound 4 was performed using Martin's sulfurane reagent to give α,β-unsaturated ester 5. This product was subjected to the 1,3-dipolar cycloaddition of diazomethane resulting in formation of bicyclic compound 6. Its pyrolysis in DMSO at 125° C. gave the expected unsaturated ester 7 which was reduced with DIBALH to the allylic alcohol 8. PDC oxidation of this compound provided the unsaturated aldehyde 9. Its reaction with (trimethylsilyl)diazomethane introduced the ethynyl substituent and afforded the desired A-ring fragment 10.

SCHEME II shows the subsequent Sonogashira coupling of the obtained A-ring dienyne 10 with an enol triflate 11 [Sanchez-Abella et al., Bioorg. Med. Chem. 16, 10244 (2008)], representing C,D-fragment derived from the protected 25-hydroxy Grundmann's ketone. The reaction should be preferentially carried out in the presence of bis(triphenylphosphine)palladium (II) acetate-copper (I) iodide catalyst and diethylamine. The coupling resulted in formation of the trienyne 12 which was further hydrogenated in the presence of Lindlar catalyst and quinoline. The expected product of such catalytic hydrogenation, previtamin D compound 13, was then subjected to the thermal reaction in hexane. The protected vitamin D compound 14 was obtained, and after hydroxyls deprotection with tetrabutylammonium fluoride provided the desired 1α,25-dihydroxy-2-methylene-vitamin $D_3$ (15). This synthetic path is described in EXAMPLE I herein.

SCHEME III shows a synthetic sequence leading to the vitamin D compounds with an "unnatural" configuration at C-20. As set forth in SCHEME III, the corresponding enol triflate 17, representing a C,D-fragment, can be easily prepared from the protected (20S)-25-hydroxy Grundmann's ketone 16 [Sicinski et al., J. Med. Chem., 41, 4662 (1998)]. Treatment of the enol form of 16, generated by addition of the LDA at –78° C., with N-phenyltriflimide afforded 17. The subsequent Sonogashira coupling of the obtained A-ring dienyne 10 with an enol triflate 17 resulted in formation of the trienyne 18 which was further hydrogenated in the presence of Lindlar catalyst and quinoline. The expected product of such catalytic hydrogenation, previtamin D compound 19, was then subjected to the thermal reaction in hexane. The protected vitamin D compound 20 was obtained, and after hydroxyls deprotection with tetrabutylammonium fluoride provided the desired (20S)-1α,25-dihydroxy-2-methylene-vitamin $D_3$ (21). This synthetic path is described in EXAMPLE II herein.

As it is evident from EXAMPLE I and EXAMPLE II, other vitamin D analogs having the different side-chains may be synthesized by the methods set forth herein.

This invention is described by the following illustrative examples. In these examples specific products identified by Arabic numerals (e.g., 1, 2, 3, etc) refer to the specific structures so identified in the preceding description and in the SCHEME I, SCHEME II and SCHEME III.

Regarding the preparation of the dienynes of the structure III, new synthetic route was established. As set forth in SCHEME I, the bicyclic keto lactone 1, efficiently prepared from commercially available (1R,3R,4S,5R)-quinic acid by the method of Glebocka et al. [J. Med. Chem., 49, 2909 (2006)] was subjected to the Wittig reaction with an ylide generated from methyltriphenylphosphonium bromide and n-butyllithium. Then, methanolysis of the formed 2 afforded ester 3 in which secondary hydroxyl was selectively protected

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 400 and 500 MHz with a Bruker DMX-400 and Bruker DMX-500 spectrometers, respectively. $^{13}$C nuclear magnetic resonance (NMR) spectra were recorded in deuteriochloroform at 100 and 125 MHz with a Bruker DMX-400 and Bruker DMX-500 spectrometers, respectively. Chemical shifts (δ) were reported downfield from internal Me$_4$Si (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

In the description of the proton MMR signals of compounds 5-10 orientation of the OTBS group, which will become 1α-OTBS and 1α-OH in the final vitamin D compounds, was arbitrarily established as "α".

Example I

Preparation of 1α,25-dihydroxy-2-methylene-vitamin D$_3$ (15).

(a) Wittig reaction of the ketone 1 (SCHEME I). (1R,3R,5R)-1-Acetoxy-3-[(tert-butyldimethylsilyl)oxy]-4-methylene-6-oxabicyclo[3.2.1]octan-7-one (2). A solution of potassium tert-butoxide in THF (1.0 M; 746 μL, 746 μmol) was added dropwise to a stirred suspension of methyl triphenylphosphonium bromide (280 mg, 784.6 mol) in anhydrous THF (5.5 mL) at 0° C. The mixture was warmed up to room temperature and stirred for additional 10 min. A solution of ketone 1 (126 mg, 382.7 mmol) in THF (1.6 mL) was added via cannula and stirring was continued at room temperature for 1 h. Water was added and the mixture was extracted with ethyl acetate, dried over MgSO$_4$ and concentrated. The residue was applied on a silica Sep-Pak cartridge and eluted with hexane/ethyl acetate (95:5) to afford compound 2 (91 mg, 73%).

2: $[\alpha]^{20}_D$ −79° (c 1.0 CHCl$_3$); $^1$H NMR (500 MHz, CDCl$_3$) δ 0.086 (6H, s, 2×SiCH$_3$), 0.921 (9H, s, Si-t-Bu), 2.06 (1H, br t, J~11 Hz, 2α-H), 2.11 (1H, d, J=11.0Hz, 8α-H), 2.14 (3H, s, OCH$_3$), 2.38 (1H, ddd, J=12.0, 7.5, 3.0Hz, 2β-H), 3.34 (1H, ddd, J=11.0, 6.5, 3.0Hz, 8β-H), 4.42 (1H, m, 3β-H), 5.15 (1H, d, J=6.5Hz, 5α-H), 5.14 (1H, br s, one of =CH$_2$), 5.25 (1H, d, J=1.5Hz, one of =CH$_2$); $^{13}$C NMR (125 MHz) δ −3.7, −3.5, 19.54, 22.57, 27.13, 42.36, 42.62, 66.07, 80.33, 112.18, 146.46, 170.61, 174.09; HRMS (ESI) exact mass calculated for C$_{16}$H$_{26}$O$_5$SiNa (M$^+$+Na) 349.1447, found 349.1451.

(b) Methanolysis of the lactone 2 and hydroxyl protection. (3R,5R)-3,5-Bis[(tert-butyldimethylsilyl)oxy]-1-hydroxy-4-methylene-cyclohexanecarboxylic acid methyl ester (4). A solution of the lactone 2 (330 mg, 1.01 mmol) was vigorously stirred in methanolic sodium methoxide solution (0.04 M; 10 mL, 0.4 mmol) at room temperature for 17 h under argon. Water was added and the mixture was extracted with ethyl acetate, dried over Na$_2$SO$_4$ and concentrated. The residue was applied on a silica Sep-Pak cartridge and eluted with hexane/ethyl acetate (7:3) to give the diol 3 (253 mg, 79%) as a colorless oil.

The diol 3 (274 mg, 865.8 μmol) was dissolved in anhydrous methylene chloride (4.5 mL) cooled to −40° C. and 2,6-lutidine (191 μL, 1.65 mmol) was added dropwise followed by tert-butyldimethylsilyl trifluoromethanesulfonate (300 μL, 1.3 mmol). The reaction mixture was stirred at −40° C. for 1 h and saturated NaHCO$_3$ was added. Cooling bath was removed and the reaction mixture was allowed to warm up slowly to room temperature. The mixture was extracted with methylene chloride, and combined organic layers were washed with 5% HCl and water, dried over Na$_2$SO$_4$ and concentrated. The residue was applied on a silica Sep-Pak cartridge and eluted with hexane/ethyl acetate (93:7) to give compound 4 (353.5 mg, 95%) as a colorless oil.

4: $[\alpha]^{20}_D$ −31.5° (c 1.0 CHCl$_3$); $^1$H NMR (400 MHz, CDCl$_3$) δ 0.084, 0.094, and 0.119 (each 3H, each s, 4×SiCH$_3$), 0.892 and 0.922 (9H and 9H, each s, 2×Si-t-Bu), 1.82 (1H, t, J~12Hz, 2α-H), 2.10 (2H, narr m, 6α- and 6β-H), 2.31 (1H, dd, J=12.4, 5.0 Hz, 2β-H), 3.75 (3H, s, COOCH$_3$), 4.69 (1H, narr m, 5α-H), 4.77 (1H, dd, J=11.2, 5.0Hz, 3β-H), 4.95 (2H, s, one of =CH$_2$ and OH), 5.16 (1H, s, one of =CH$_2$); $^{13}$C NMR (100 MHz) δ −5.41, −5.05, −4.94, −4.90, 17.75, 18.17, 25.54, 25.76, 40.78, 46.53, 52.45, 65.93, 75.15, 108.43, 150.18, 173.72; HRMS (ESI) exact mass calculated for C$_{21}$H$_{42}$O$_5$Si$_2$Na (M$^+$+Na) 453.2469, found 453.2458.

(c) Dehydration of hydroxy ester 4 (3R,5R)-3,5-Bis[(tert-butyldimethylsilyl)oxy]-4-methylene-cyclohex-1-enecarboxylic acid methyl ester (5). To a stirred solution of alcohol 4 (326 mg, 756.8 μmol) in anhydrous carbon tetrachloride (8.2 mL) was added a solution of bis[α,α-bis(trifluoromethyl)benzyloxy]diphenylsulfur (752 mg, 1.12 mmol) in anhydrous carbon tetrachloride (6 mL) at room temperature under argon. Reaction was stirred for 30 min, and water was added. The mixture was extracted with methylene chloride, dried over Na$_2$SO$_4$ and concentrated. The resulting residue was applied on a silica Sep-Pak cartridge and eluted with hexane/diethyl ether (98:2) to give the desired product contaminated by dehydrating reagent. Further purification on preparative TLC plates (Silica Gel 60F$_{254}$, 20×20 cm, layer thickness 250 nm) using hexane/diethyl ether (92:8) afforded unsaturated ester 5 (276 mg, 90%) as a colorless oil.

5: $[\alpha]^{20}_D$ −106° (c 1.0 CHCl$_3$); $^1$H NMR (500 MHz, CDCl$_3$) δ 0.057, 0.075, 0.099, and 0.129 (each 3H, each s, 4×SiCH$_3$), 0.885 and 0.917 (9H and 9H, each s, 2×Si-t-Bu), 2.33 (1H, dd, J=17.5, 6.0Hz, 6β-H), 2.68 (1H, ddd, J=17.5, 3.0, 2.0Hz, 6α-H), 3.74 (3H, s, COOCH$_3$), 4.57 (1H, t, J~5Hz, 5α-H), 4.92 (1H, br s, 3β-H), 5.03 and 5.09 (1H and 1H, each s, =CH$_2$), 6.75 (1H, narr m, 2-H); $^{13}$C NMR (125 MHz) δ −5.03, −4.91, −4.83, −4.78, 18.17, 18.26, 25.74, 25.80, 36.71, 51.87, 68.93, 69.46, 108.82, 129.28, 139.63, 148.78, 167.27; HRMS (ESI) exact mass calculated for C$_{21}$H$_{40}$O$_4$Si$_2$Na (M$^+$+Na) 435.2363, found 435.2364.

(d) Addition of diazomethane to the ester 5. (3aR,4R,6R,7aR)-4,6-Bis[(tert-butyldimethylsilyl)oxy]-5-methylene-3,3a,4,5,6,7-hexahydro-indazole-7a-carboxylic acid methyl ester (6). Solution of diazomethane in diethyl ether [2.7 mL; prepared according to the procedure of Arndt, Org. Synth., 15, 3, 48 (1935)] was added to a solution of the ester 5 (264 mg, 639.7 mol) in anhydrous ethyl ether (1 mL) at room temperature. Reaction mixture was protected from light and stirred for 2 h. Solvent was evaporated, a residue dissolved in hexane, applied on a silica Sep-Pak cartridge and eluted with hexane/ethyl acetate (97:3) to give bicyclic adduct 6 (288 mg, 99%) as a colorless oil.

6: $[\alpha]^{20}_D$ −142° (c 1.0 CHCl$_3$); $^1$H NMR (500 MHz, CDCl$_3$) δ 0.012, 0.052, 0.056, and 0.096 (each 3H, each s, 4×SiCH$_3$), 0.857 and 0.921 (9H and 9H, each s, 2×Si-t-Bu), 1.28 (1H, dd, J=14.0, 3.0Hz, 7β-H), 2.85 (1H, dd, J=14.0, 4.5Hz, 7α-H), 2.92 (1H, m, 3α-H), 3.84 (3H, s, COOCH$_3$), 4.05 (1H, dd, J=17.7, 10.0Hz, one of =N—CH$_2$), 4.38 (1H, t, J=4.0Hz, 6α-H), 4.75 (1H, dd, J=17.7, 8.0Hz, one of =N—CH$_2$), 4.90 (1H, d, J=6.5Hz, 4β-H), 4.97 and 5.10 (1H and 1H, each s, =CH$_2$); $^{13}$C NMR (125 MHz) δ −5.16, −5.08, −4.95, 17.96, 18.14, 25.52, 25.71, 38.17, 41.95, 52.95, 66.85, 72.17, 94.55, 110.41, 147.26, 170.35; HRMS (ESI) exact mass calculated for C$_{22}$H$_{42}$O$_4$N$_2$Si$_2$Na (M$^+$+Na) 477.2581, found 477.2573.

(e) Pyrolysis of the adduct 6. (3R,5R)-3,5-Bis[(tert-butyldimethylsilyl)oxy]-2-methyl-4-methylene-cyclohex-1-enecarboxylic acid methyl ester (7). A solution of compound 6 (14 mg, 32.54 mol) in freshly distilled anhydrous DMSO (0.6 mL) was stirred at 125° C. for 32 h under argon. Heating bath was removed, water was added and the mixture was extracted with hexane, dried over $Na_2SO_4$ and concentrated. The crude product was applied on a silica Sep-Pak cartridge and eluted with hexane/diethyl ether (97:3) to afford unsaturated ester 7 (9 mg, 65%).

7: $[\alpha]^{20}_D$ −87° (c 1.0 $CHCl_3$); $^1H$ NMR (400 MHz, $CDCl_3$) δ 0.070, 0.087, and 0.134 (6H, 3H and 3H, each s, 4×$SiCH_3$), 0.879 and 0.920 (9H and 9H, each s, 2×Si-t-Bu), 2.04 (3H, s, $CH_3$), 2.16 (1H, m, one of 6-$H_2$), 2.76 (1H, dd, J=17.2, 5.0Hz, one of 6-$H_2$), 3.73 (3H, s, COOCH$_3$), 4.32 (1H, s, 3β-H), 4.55 (1H, t, J~7Hz, 5α-H), 4.93 and 5.18 (1H and 1H, each s, =$CH_2$); $^{13}C$ NMR (100 MHz) δ −4.90, −4.83, −4.14, 18.09, 18.20, 18.73, 25.73, 25.83, 38.98, 51.44, 67.05, 71.91, 108.32, 124.60, 145.15, 149.98, 168.59; HRMS (ESI) exact mass calculated for $C_{22}H_{42}O_4Si_2Na$ ($M^+$+Na) 449.2519, found 449.2521.

(f) Reduction of the ester 7. [(3'R,5'R)-3',5'-Bis[(tert-butyldimethylsilyl)oxy]-2'-methyl-4'-methylene-cyclohex-1'-enyl]-methanol (8). Diisobutylaluminum hydride (1.0 M in toluene; 260 μL, 260 mmol) was slowly added to a stirred solution of the ester 7 (25 mg, 58.6 μmol) in toluene/methylene chloride (2:1; 3 mL) at −78° C. under argon. Stirring was continued at −78° C. for 2 h. The mixture was quenched by the slow addition of potassium-sodium tartrate (2N, 4 mL), aqueous HCl (2N, 4 mL) and $H_2O$ (16 mL) and extracted with ethyl acetate. The combined organic layers were washed with brine, dried over $MgSO_4$ and concentrated. The residue was applied on a silica Sep-Pak cartridge and eluted with hexane/ethyl acetate (98:2) to give the alcohol 8 (14 mg, 60%).

8: $[\alpha]^{20}_D$ −89° (c 1.0 $CHCl_3$); $^1H$ NMR (400 MHz, $CDCl_3$) δ 0.043, 0.070, 0.081, and 0.125 (each 3H, each s, 4×$SiCH_3$), 0.879 and 0.919 (9H and 9H, each s, 2×Si-t-Bu), 1.76 (3H, s, $CH_3$), 2.10 (1H, dd, J=16.1, 9.6Hz, 6β-H), 2.58 (1H, dd, J=16.1, 6.0Hz, 6α-H), 4.11 (2H, s, $CH_2$—OH), 4.38 (1H, s, 3β-H), 4.57 (1H, t, J~8Hz, 5α-H), 4.90 and 5.15 (1H and 1H, each s, =$CH_2$); $^{13}C$ NMR (100 MHz) δ −4.86, −4.82, −4.69, 15.89, 18.17, 18.22, 25.83, 25.86, 40.30, 62.86, 67.69, 76.34, 107.62, 131.14, 132.30, 151.13; HRMS (ESI) exact mass calculated for $C_{21}H_{42}O_3Si_2Na$ ($M^+$+Na) 421.2570, found 421.2572.

(g) Oxidation of alcohol 8. (3R,5R)-3,5-Bis[(tert-butyldimethylsilyl)oxy]-2-methyl-4-methylene-cyclohex-1-enecarbaldehyde (9). The mixture of alcohol 8 (16 mg, 40.2 mol) and pyridinium dichromate (48.5 mg, 225.1 mol) in anhydrous methylene chloride (0.7 mL) was stirred vigorously at room temperature for 4 h. The reaction mixture was then filtered through a pad of Celite (washed with methylene chloride) and the solvents were removed under reduced pressure. The crude product was applied on a silica Sep-Pak cartridge and eluted with hexane/diethyl ether (98:2) to yield the aldehyde 9 (12.6 mg, 79%) as a colorless oil.

9: $[\alpha]^{20}_D$ −112° (c 1.0 $CHCl_3$); $^1H$ NMR (400 MHz, $CDCl_3$) δ 0.066, 0.085, 0.094, and 0.168 (each 3H, each s, 4×$SiCH_3$), 0.908 (18H, s, 2×Si-t-Bu), 2.02 (1H, dd, J=17.0, 7.1Hz, 6β-H), 2.20 (3H, s, $CH_3$), 2.78 (1H, dd, J=17.0, 5.5Hz, 6α-H), 4.52 (1H, t, J~6.5Hz, 5α-H), 4.58 (1H, s, 3β-H), 4.99 and 5.21 (1H and 1H, each s, =$CH_2$), 10.11 (1H, s, CHO); $^{13}C$ NMR (100 MHz) δ −4.94, −4.81, −4.15, 14.99, 18.13, 25.73, 25.80, 35.16, 67.51, 75.93, 108.97, 132.40, 149.55, 153.67, 191.66; HRMS (ESI) exact mass calculated for $C_{21}H_{40}O_3Si_2Na$ ($M^+$+Na) 419.2414, found 419.2417.

(h) Transformation of the aldehyde 9 to the dienyne 10. (3R,5R)-3,5-Bis[(tert-butyldimethylsilyl)oxy]-1-ethynyl-2-methyl-4-methylene-cyclohexene (10). n-BuLi (1.6 M in hexanes; 25.5 μL, 40.8 mol) was added to a solution of (trimethylsilyl)diazomethane (2.0 M in hexane, 19.5 μL, 39 mol) in anhydrous THF (50 μL) at −78° C. under argon, and a solution of aldehyde 9 (12.6 mg, 31.8 μmol) in dry THF (100 μL+50 μL) was added via cannula. After 1 h the cooling bath was removed and stirring was continued at room temperature overnight. Water was added, and the mixture was extracted with hexane, dried over $Na_2SO_4$ and concentrated. The crude product was applied on a silica Sep-Pak cartridge and eluted with hexane to afford dienyne 10 (10 mg, 82%).

10: $[\alpha]^{20}_D$ −102° (c 1.0 $CHCl_3$); $^1H$ NMR (400 MHz, $CDCl_3$) δ 0.060, 0.067, 0.078, and 0.126 (each 3H, each s, 4×$SiCH_3$), 0.880 and 0.913 (9H and 9H, each s, 2×Si-t-Bu), 1.95 (3H, s, $CH_3$), 2.15 (1H, br m, 6β-H), 2.55 (1H, dd, J=17.5, 6.3Hz, 6α-H), 3.07 (1H, s, ≡CH), 4.46 (1H, s, 3β-H), 4.55 (1H, ddt, J=8.8, 6.3, ca. 2Hz, 5α-H), 4.94 (1H, br s, one of =$CH_2$), 5.16 (1H, t, J=1.9Hz, one of =$CH_2$); $^{13}C$ NMR (100 MHz) δ −4.91, −4.78, −4.20, 18.12, 18.21, 25.74, 25.81, 41.88, 67.02, 74.79, 79.97, 83.26, 108.33, 114.71, 143.62, 150.07; HRMS (ESI) exact mass calculated for $C_{22}H_{40}O_2Si_2Na$ ($M^+$+Na) 415.2465, found 415.2455.

(i) Coupling of dienyne 10 with the triflate 11 (SCHEME II). 1α,3β-Bis[(tert-butyldimethylsilyl)oxy]-2-methylene-25-[(triethylsilyl)oxy]-9,10-secocholesta-5(10),8-dien-6-yne (12). To a solution of dienyne 10 (8 mg, 20.4 μmol) and triflate 11 (8.4 mg, 15.9 mol) in anhydrous DMF (200 μL) were added CuI (0.45 mg, 2.37 μmol), $(PPh_3)_2Pd(OAc)_2$ (0.34 mg, 0.45 mol) and $Et_2NH$ (159 μL) at room temperature under argon. After 45 min the mixture turned deep reddish-brown. Water was added and the mixture was extracted with hexane, dried over $MgSO_4$ and concentrated. The resulting product was applied on a silica Sep-Pak cartridge and eluted with hexane to afford trienyne 12 (8.3 mg, 92%) and recovered acetylene 10 (2.2 mg).

12: $^1H$ NMR (400 MHz, $CDCl_3$) δ 0.051, 0.062, 0.072, and 0.116 (each 3H, each s, 4×$SiCH_3$), 0.562 (6H, q, J=7.8Hz, 3×$SiCH_2$), 0.698 (3H, s, 18-$H_3$), 0.870 and 0.912 (9H and 9H, each s, 2×Si-t-Bu), 0.918 (3H, d, J=6.1Hz, 21-$H_3$), 0.945 (9H, t, J=7.8 Hz, 3×$SiCH_2CH_3$), 1.18 (6H, s, 26- and 27-$H_3$), 1.92 (3H, s, $CH_3$), 2.53 (1H, dd, J=16.6, 6.0Hz), 4.45 (1H, s, 1β-H), 4.56 (1H, t, J~7.5Hz, 3α-H), 4.91 and 5.14 (1H and 1H, each s, =$CH_2$), 5.97 (1H, narr m, 9-H); HRMS (ESI) exact mass calculated for $C_{46}H_{84}O_3Si_3Na$ ($M^+$+Na) 791.5626, found 791.5637.

(j) Hydrogenation of the trienyne 12 and thermal reaction of previtamin D compound 13. 1α-[(tert-Butyldimethylsilyl)oxy]-2-methylene-25-[(triethylsilyl)oxy]-vitamin $D_3$ tert-butyldimethylsilyl ether (14). To a solution of the trienyne 12 (8.3 mg, 10.8 mol) in hexane (3 mL) and quinoline (2 μL) was added Lindlar catalyst (25 mg) and the mixture was stirred at room temperature under a positive pressure of hydrogen. Lindlar catalyst was added twice during 2.5 h (in 20 mg portions) and then the mixture was applied on a silica Sep-Pak cartridge and eluted with hexane/ether (98:2) to give the silylated previtamin 13 (5.8 mg, 70%). The previtamin was then dissolved in anhydrous hexane (3 mL) and stirred at 60° C. for 14 h under argon. Solvent was evaporated and residue was applied on a silica Sep-Pak cartridge and eluted with hexane/diethyl ether (99.6:0.4) to give protected vitamin 14 (5.8 mg, 100%).

14: $^1H$ NMR (500 MHz, $CDCl_3$) δ 0.055, 0.059, 0.074, and 0.082 (each 3H, each s, 4×$SiCH_3$), 0.538 (3H, s, 18-$H_3$), 0.562 (6H, q, J=7.5Hz, 3×$SiCH_2$), 0.890 (18H, s, 2×Si-t-Bu), 0.922 (3H, d, J=6.5Hz, 21-$H_3$), 0.945 (9H, t, J=7.5, 3×SiCH$_2$CH$_3$), 1.18 (6H, s, 26- and 27-H$_3$), 2.26 (1H, dd, J=13.0, 7.0Hz, 4β-H), 2.50 (1H, dd, J=13.0, 4.5Hz, 4α-H), 2.83 (1H, br d, J=13.5Hz, 9β-H), 4.55 (1H, m, 3α-H), 4.72 (1H, s, 1β-H), 4.85, 4.95, 4.98 and 5.23 (each 1H, each s, 2×=CH$_2$), 6.04 and 6.29 (1H and 1H, each d, J=11.0Hz, 7- and 6-H); HRMS (ESI) exact mass calculated for C$_{46}$H$_{86}$O$_3$Si$_3$Na (M+Na) 793.5782, found 793.5778.

(k) Deprotection of hydroxyls in the vitamin D compound 14. 1α,25-Dihydroxy-2-methylene-vitamin D$_3$ (15). To a solution of protected vitamin 14 (5.8 mg, 7.52 µmol) in THF (1 mL) was added tetrabutylammonium fluoride (1.0 M in THF; 450 µL, 450 µmol) at room temperature under argon. The stirring was continued for 20 h, brine was added and the mixture was extracted with ethyl acetate. The organic extracts were dried over MgSO$_4$ and evaporated. The residue was purified by HPLC (9.4 mm×25 cm Zorbax-Sil column, 4 mL/min) using hexane/2-propanol (9:1) solvent system; vitamin 15 (1.28 mg, 40%) was collected at R$_V$ 36 mL. Analytical sample of the vitamin was obtained after HPLC (9.4 mm×25 cm Zorbax Eclipse XDB-C18 column, 4 mL/min) using methanol/water (88:12) solvent system (R$_V$ 33 mL).

15: UV (EtOH) λ$_{max}$ 269.0 nm; $^1$H NMR (500 MHz, CDCl$_3$) δ 0.551 (3H, s, 18-H$_3$), 0.939 (3H, d, J=6.5Hz, 21-H$_3$), 1.218 (6H, s, 26- and 27-H$_3$), 2.39 (1H, dd, J=13.3, 6.5Hz, 4β-H), 2.67 (1H, dd, J=13.3, 3.8Hz, 4α-H), 2.83 (1H, br d, J=12.7, 9β-H), 4.61 (1H, m, 3α-H), 4.87 (1H, br s, 1β-H), 5.02, 5.11, 5.16, and 5.39 (each 1H, each s, 2×=CH$_2$), 6.07 and 6.44 (1H and 1H, each d, J=11.5Hz, 7- and 6-H); HRMS (ESI) exact mass calculated for C$_{28}$H$_{44}$O$_3$Na (M$^+$+Na) 451.3188, found 451.3177.

Example II

Preparation of (20S)-1α,25-dihydroxy-2-methylene-vitamin D$_3$ (21) and (5E)-(20S)-1α,25-dihydroxy-2-methylene-vitamin D$_3$ (22).

(a) Conversion of the Grundmann ketone 16 to the enol triflate 17 (SCHEME III). (20S)-25-[(Triethylsilyl)oxy]-8-trifluoromethanesulfonyloxy-des-A,B-cholest-8-ene (17). A solution of the ketone 16 (28.5 mg, 72.19 mol) in anhydrous THF (350 µL) was slowly added to the solution of LDA (2.0 M in THF/heptane/ethylbenzene; 40 µL, 80 µmol) in dry THF (100 µL) at −78° C. under argon. Then a solution of N-phenyltriflamide (28.3 mg, 79.27 µmol) in dry THF (100 µL) was added. After 2 h cooling bath was removed and reaction mixture was allowed to warm up to room temperature. Stirring was continued for 30 min and water was added. The mixture was extracted with hexane, dried over MgSO$_4$ and concentrated. The residue was applied on a silica Sep-Pak cartridge and eluted with hexane to afford the enol triflate 17 (17.2 mg, 82% considering recovered substrate) and unreacted ketone 16 (12 mg).

16: [α]$^{20}$$_D$ −5.3° (c 0.86 CHCl$_3$); $^1$H NMR (200 MHz, CDCl$_3$) δ 0.564 (6H, q, J=8Hz, 3×SiCH$_2$), 0.762 (3H, s, 18-H$_3$), 0.855 (3H, d, J=6.4Hz, 21-H$_3$), 0.944 (9H, t, J=7.6Hz, 3×SiCH$_2$CH$_3$), 1.18 (6H, s, 26- and 27-H$_3$), 1.789 (1H, m), 1.97 (2H, m), 2.30 (2H, m), 2.48 (1H, m), 5.66 (1H, dd, J=6.8, 3.4Hz, 9-H); $^{13}$C NMR (50 MHz, CDCl$_3$) δ 6.98, 7.30, 11.68, 18.74, 20.83, 21.54, 24.07, 28.43, 30.02, 30.11, 35.01, 35.68, 35.94, 45.62, 50.36, 54.03, 73.54, 116.18, 150.16; HRMS (ESI) exact mass calculated for C$_{25}$H$_{45}$F$_3$O$_4$SSiNa (M$^+$+Na) 549.2658, found 549.2637.

(b) Coupling of dienyne 10 with the triflate 17. (20S)-1α, 3β-Bis[(tert-butyldimethylsilyl)oxy]-2-methylene-25-[(triethylsilyl)oxy]-9,10-secocholesta-5(10),8-dien-6-yne (18). To a solution of dienyne 10 (15.5 mg, 39.54 mmol) and triflate 17 (12.5 mg, 27.73 mol) in anhydrous DMF (240 µL) were added CuI (0.67 mg, 3.52 µmol), (PPh$_3$)$_2$Pd(OAc)$_2$ (0.50 mg, 0.67 mol) and Et$_2$NH (240 µL) at room temperature under argon. After 45 min the mixture turned deep reddish-brown. Water was added and the mixture was extracted with hexane, dried over MgSO$_4$ and concentrated. The resulting product was applied on a silica Sep-Pak cartridge and eluted with hexane to afford trienyne 18 (10.3 mg, 54%) and recovered dienyne 10 (5.7 mg).

18: $^1$H NMR (500 MHz, CDCl$_3$) δ 0.051, 0.062, 0.074, and 0.117 (each 3H, each s, 4×SiCH$_3$), 0.561 (6H, q, J=8Hz, 3×SiCH$_2$), 0.697 (3H, s, 18-H$_3$), 0.872 and 0.913 (9H and 9H, each s, 2×Si-t-Bu), 0.93 (3H, 21-H$_3$), 0.942 (9H, t, J=8Hz, 3×SiCH$_2$CH$_3$), 1.186 (6H, s, 26- and 27-H$_3$), 1.92 (3H, s, CH$_3$), 2.53 (1H, dd, J=16, 7.5Hz), 4.46 (1H, s, 1β-H), 4.56 (1H, t, J~7Hz, 3α-H), 4.91 and 5.14 (1H and 1H, each s, =CH$_2$), 5.97 (1H, narr m, 9-H); HRMS (ESI) exact mass calculated for C$_{46}$H$_{84}$O$_3$Si$_3$Na (M$^+$+Na) 791.5626, found 791.5638.

(c) Hydrogenation of the trienyne 18 and thermal reaction of previtamin D compound 19. (20S)-1α-[(tert-Butyldimethylsilyl)oxy]-2-methylene-25-[(triethylsilyl)oxy]-vitamin D$_3$ tert-butyldimethylsilyl ether (20). To a solution of the trienyne 18 (9 mg, 11.7 µmol) in hexane (1.3 mL) and quinoline (2.2 µL) was added Lindlar catalyst (31 mg) and the mixture was stirred at room temperature under a positive pressure of hydrogen. After 45 min the mixture was applied on a silica Sep-Pak cartridge and eluted with hexane/ether (99:1) to give the silylated previtamin 19 (7.6 mg, 84%). The previtamin was then dissolved in anhydrous hexane (6 mL) and stirred at 60° C. for 19 h under argon. Solvent was evaporated and residue was applied on a silica Sep-Pak cartridge and eluted with hexane/diethyl ether (99.6:0.4) to give protected vitamin 20 (6.3 mg, 70%).

20: $^1$H NMR (500 MHz, CDCl$_3$) δ 0.054, 0.059, 0.069, and 0.082 (each 3H, each s, 4×SiCH$_3$), 0.534 (3H, s, 18-H$_3$), 0.563 (6H, q, J=8Hz, 3×SiCH$_2$), 0.883 (3H, d, J=6.5Hz, 21-H$_3$), 0.891 (18H, s, 2×Si-t-Bu), 0.944 (9H, t, J=8Hz, 3×SiCH$_2$CH$_3$), 1.187 (6H, s, 26- and 27-H$_3$), 2.26 (1H, dd, J=12.5, 7.0Hz, 4β-H), 2.50 (1H, dd, J=12.5, 4.5Hz, 4α-H), 2.83 (1H, br d, J=12.5Hz, 9β-H), 4.55 (1H, dd, J=7.0, 4.5Hz, 3α-H), 4.72 (1H, s, 1β-H), 4.85, 4.95, 4.99, and 5.23 (each 1H, each s, 2×=CH$_2$), 6.04 and 6.29 (1H and 1H, each d, J=11.0Hz, 7- and 6-H); HRMS (ESI) exact mass calculated for C$_{46}$H$_{86}$O$_3$Si$_3$Na (M$^+$+Na) 793.5782, found 793.5788.

(d) Deprotection of hydroxyls in the vitamin D compound 20. (20S)-1α,25-Dihydroxy-2-methylene-vitamin D$_3$ (21). To a solution of protected vitamin 20 (6.3 mg, 8.17 µmol) in THF (1 mL) was added tetrabutylammonium fluoride (1.0 M in THF; 750 µL, 750 µmol) at room temperature under argon. The stirring was continued for 20 h, brine was added and the mixture was extracted with ethyl acetate. The organic extracts were dried over MgSO$_4$ and evaporated. The residue was purified by HPLC (9.4 mm×25 cm Zorbax-Sil column, 4 mL/min) using hexane/2-propanol (92:8) solvent system; vitamin 21 (567 µg, 16%) was collected at R$_V$ 36 mL. Analytical sample of the vitamin was obtained after HPLC (9.4 mm×25 cm Zorbax Eclipse XDB-C18 column, 4 mL/min) using methanol/water (88:12) solvent system ($R_V$ 30 mL).

21: UV (EtOH) $\lambda_{max}$ 270.0 nm; $^1$H NMR (500 MHz, CDCl$_3$) δ 0.549 (3H, s, 18-H$_3$), 0.852 (3H, d, J=6.5Hz, 21-H$_3$), 1.215 (6H, s, 26- and 27-H$_3$), 2.39 (1H, dd, J=13.7, 6.5Hz, 4β-H), 2.66 (1H, dd, J=13.7, 4.0Hz, 4α-H), 2.83 (1H, br d, J=12.0Hz, 9β-H), 4.61 (1H, ~q, J=5.5Hz, 3α-H), 4.87 (1H, br d, J~5.5Hz, 1β-H), 5.018, 5.108, 5.159, and 5.397 (each 1H, each s, 2×=CH$_2$), 6.07 and 6.43 (1H and 1H, each d, J=11.5Hz, 7- and 6-H); HRMS (ESI) exact mass calculated for C$_{28}$H$_{44}$O$_3$Na (M$^+$+Na) 451.3188, found 451.3174.

(e) The isomerization of (5Z)-vitamin 21 to the respective (5E)-isomer 22 can be accomplished by the well-known procedure [Having a et al., Rec. Trav. Chim. 78, 1004 (1959)] using iodine as a catalyst. Analytical sample of the vitamin was obtained after HPLC (9.4 mm×25 cm Zorbax Eclipse XDB-C18 column, 4 mL/min) using methanol/water (84:16) solvent system ($R_V$ 55 mL).

22: UV (EtOH) $\lambda_{max}$ 278.0 nm; $^1$H NMR (500 MHz, CDCl$_3$) δ 0.567 (3H, s, 18-H$_3$), 0.869 (3H, d, J=6.0Hz, 21-H$_3$), 1.217 (6H, s, 26- and 27-H$_3$), 2.38 (1H, dd, J=14.0, 9.0Hz, 4β-H), 2.86 (1H, br d, J=13.5Hz, 9β-H), 2.93 (1H, dd, J=14.0, 4.5Hz, 4α-H), 4.64 (1H, m, 3α-H), 4.89 (1H, d, J=4.5Hz, 1β-H), 5.05 and 5.15 (each 1H, each s, 2×=CH$_2$), 5.17 and 5.18 (each 1H, each d, J=1Hz, 2×=CH$_2$), 5.90 and 6.55 (1H and 1H, each d, J=11.5Hz, 7- and 6-H); HRMS (ESI) exact mass calculated for C$_{28}$H$_{44}$O$_3$Na (M$^+$+Na) 451.3188, found 451.3193.

SCHEME I, SCHEME II and SCHEME III are set forth below.

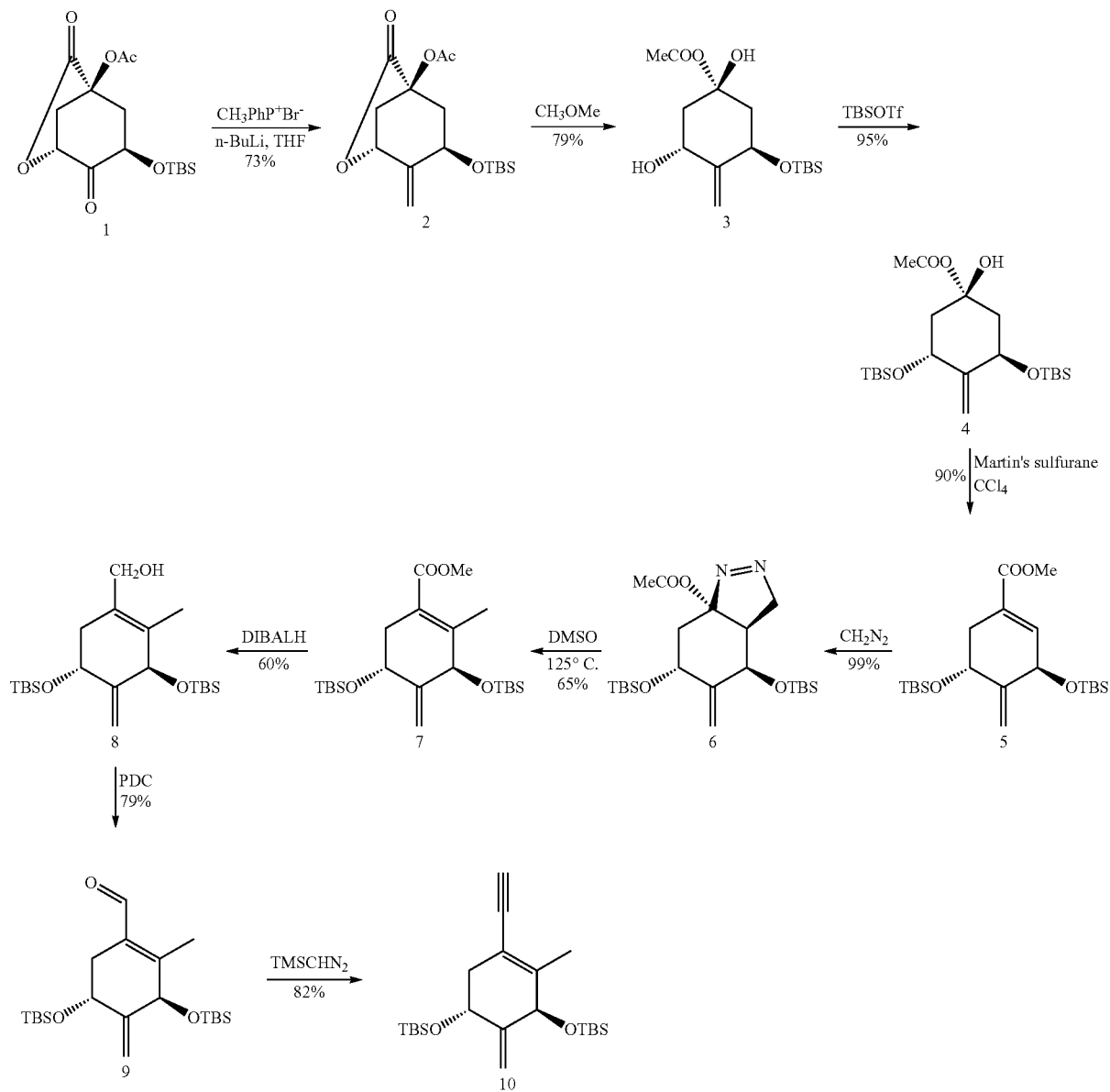

SCHEME I

SCHEME II
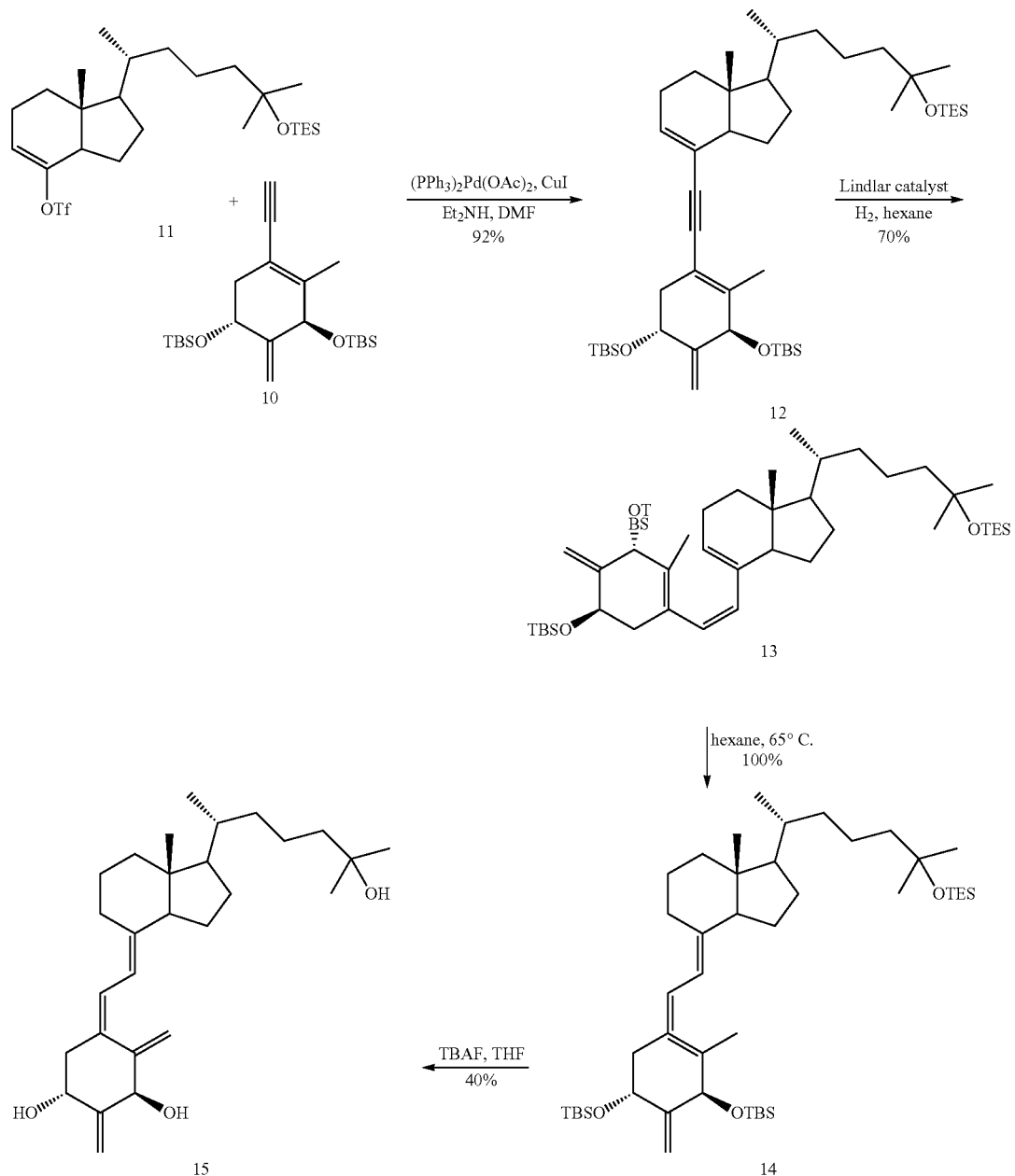

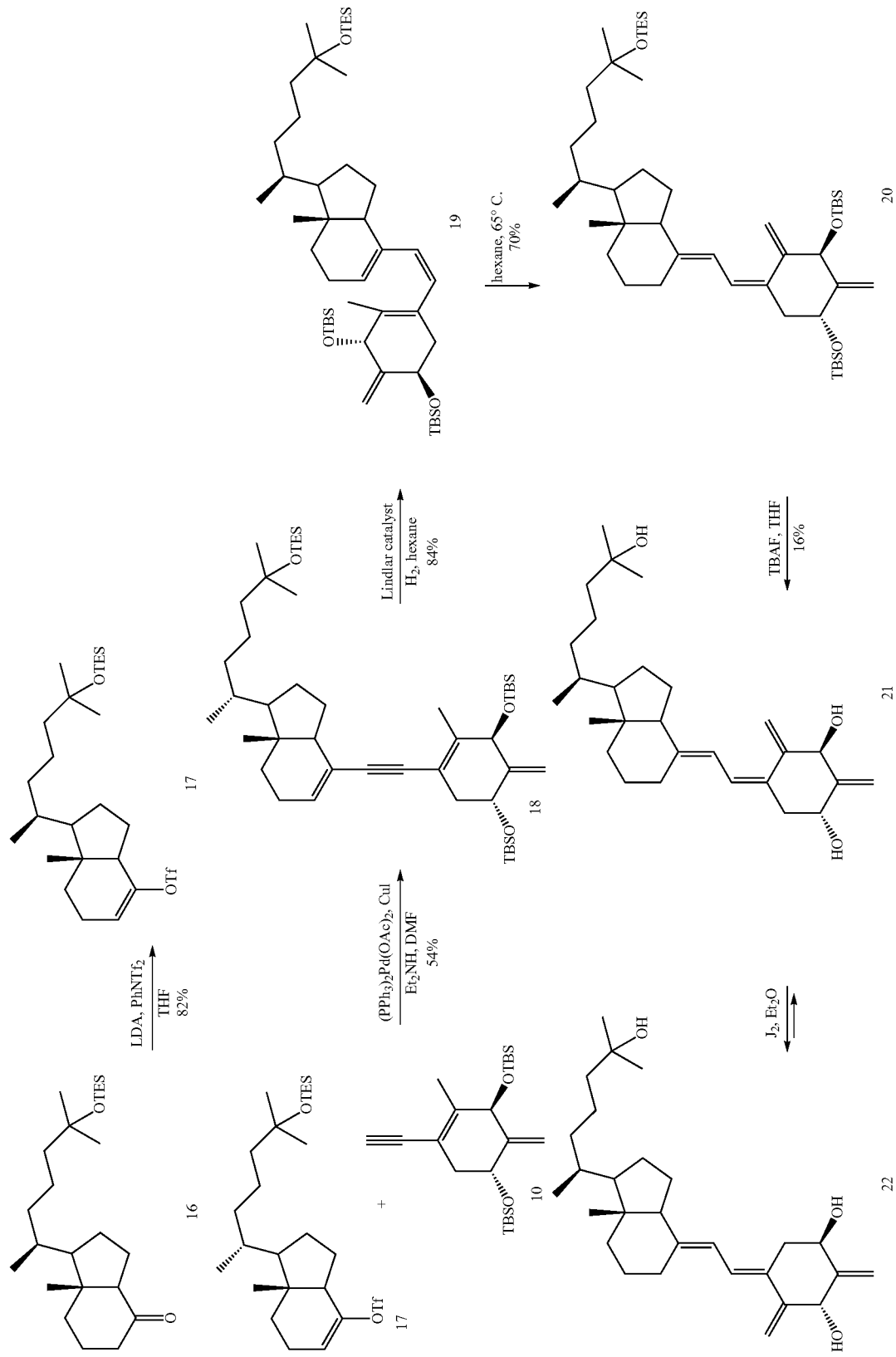

Biological Activity of (20S)-1α,25-Dihydroxy-2-Methylene-Vitamin D$_3$ (2EG-S)

The introduction of a methylene group to the 2-position, retaining the methylene substituent at carbon 10, and orienting the methyl group at carbon 20 in its epi or S configuration had little or no effect on binding to the full length recombinant rat vitamin D receptor, as compared to 1α,25-dihydroxyvitamin D$_3$. The compound 2EG-S bound with about the same affinity to the receptor as compared to the standard 1,25-(OH)$_2$D$_3$ (FIG. 1). It might be expected from these results that compound 2EG-S would have equivalent biological activity. Surprisingly, however, compound 2EG-S is a highly selective analog with unique biological activity.

Figure 5:
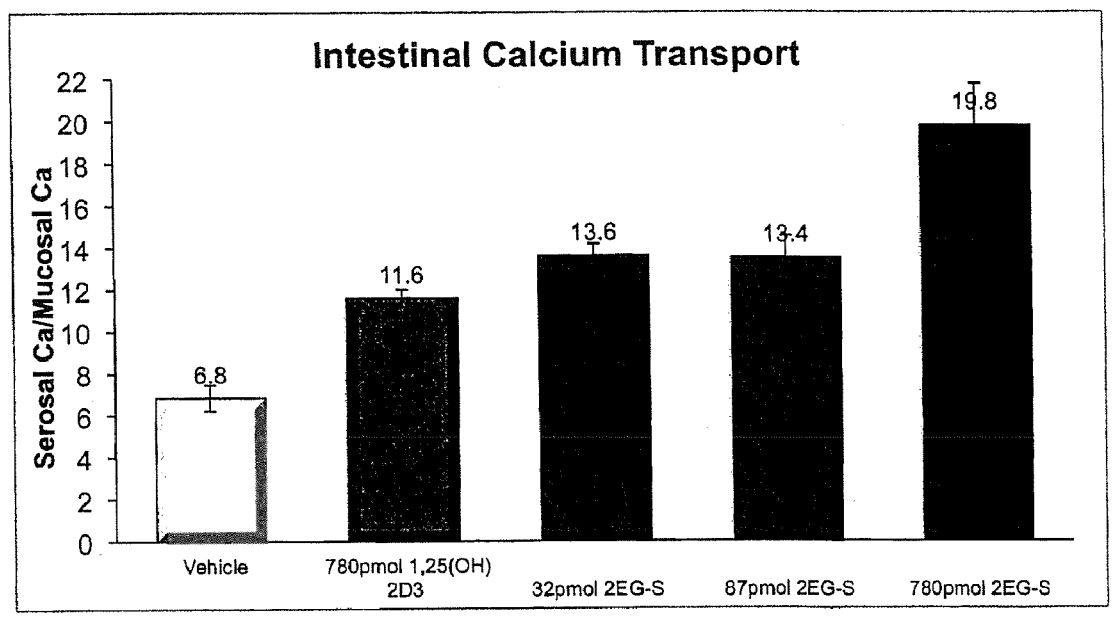

FIG. 5 shows that 2EG-S has relatively high activity as compared to that of 1,25-dihydroxyvitamin D$_3$ (1,25(OH)$_2$D$_3$), the natural hormone, in stimulating intestinal calcium transport. 2EG-S is more potent than 1,25(OH)$_2$D$_3$ in promoting active calcium transport across the gut.

Figure 4:
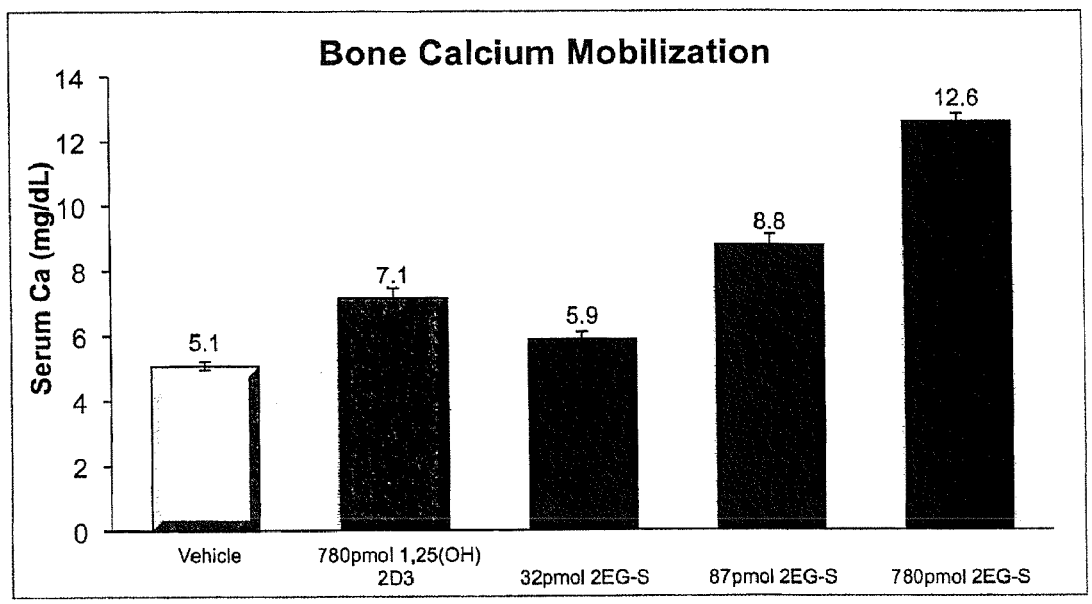

FIG. 4 demonstrates that 2EG-S has relatively high bone calcium mobilization activity, as compared to 1,25(OH)$_2$D$_3$. 2EG-S is more potent than the native hormone in releasing bone calcium stores.

FIGS. 4-5 thus illustrate that 2EG-S may be characterized as having relatively high calcemic activity.

Figure 2:
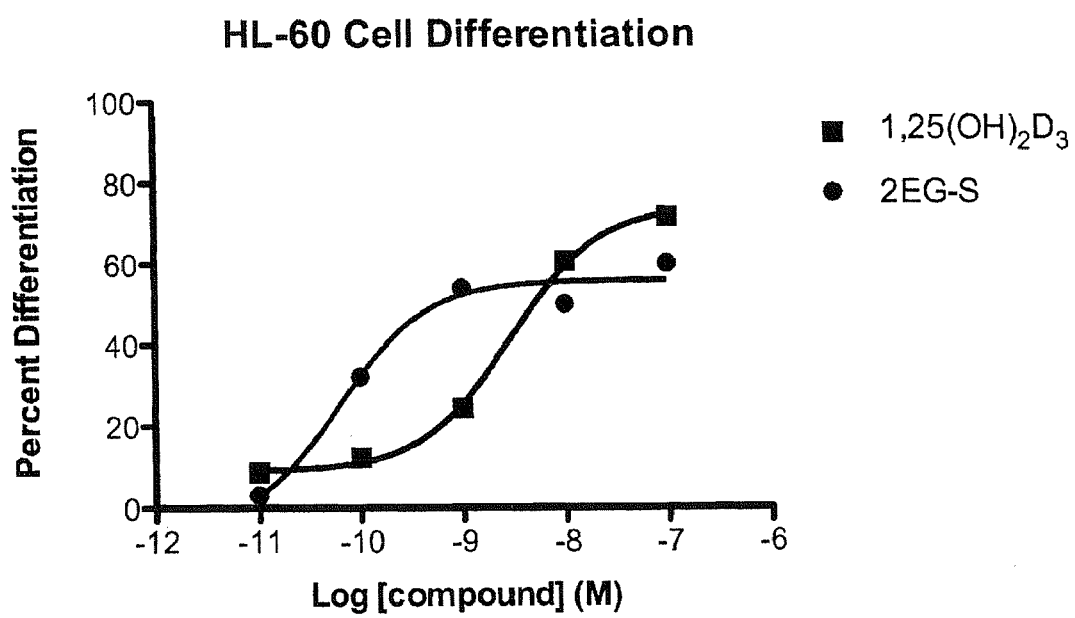

FIG. 2 illustrates that 2EG-S is more potent than 1,25(OH)$_2$D$_3$ on HL-60 cell differentiation, making it an excellent candidate for the treatment of a cancer, especially for the prevention or treatment of osteosarcoma, leukemia, colon cancer, breast cancer, skin cancer and prostate cancer.

Figure 3:
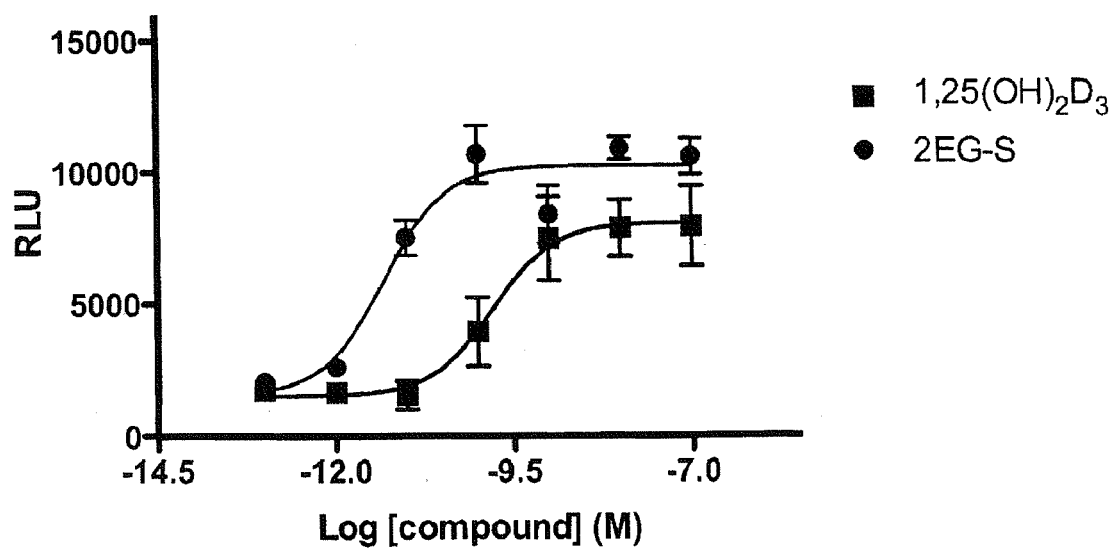

FIG. 3 illustrates that the compound 2EG-S has greater transcriptional activity than 1α,25-dihydroxyvitamin D$_3$ in bone cells. In bone cells, 2EG-S is about 40 times more potent than 1,25(OH)$_2$D$_3$ in increasing transcription of the 24-hydroxylase gene. This result, together with the cell differentiation activity of FIG. 2, suggests that 2EG-S will be very effective in treating the above referred to cancers because it has direct cellular activity in causing cell differentiation, gene transcription, and in suppressing cell growth.

Experimental Methods

The compounds of the invention were prepared and studied using the following methods.

Vitamin D Receptor Binding

Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25(OH)$_2$D$_3$: molar extinction coefficient=18,200 and $\lambda_{max}$=265 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR Binding, HL60 Cell Differentiation, and Transcription Activity.

2EG-S ($K_i=1\times10^{-10}$ M) has about the same activity as the natural hormone 1α,25-dihydroxyvitamin $D_3$ ($K_i=1\times10^{-10}$ M) in its ability to compete with [$^3$H]-1,25(OH)$_2$D$_3$ for binding to the full-length recombinant rat vitamin D receptor (FIG. 1). 2EG-S is also more potent ($EC_{50}=6\times10^{-11}$M) in its ability (efficacy or potency) to promote HL60 differentiation as compared to 1α,25-dihydroxyvitamin $D_3$ ($EC_{50}=3\times10^{-9}$ M) (See FIG. 2). Also, compound 2EG-S ($EC_{50}=5\times10^{-12}$M) has about 40 times more transcriptional activity in bone cells than 1α,25-dihydroxyvitamin $D_3$ ($EC_{50}=2\times10^{-10}$ M) (See FIG. 3). These data indicate that 2EG-S will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D-Deficient Animals.

Using vitamin D-deficient rats on a low calcium diet (0.02%), the activities of 2EG-S and 1,25(OH)$_2$D$_3$ in intestine and bone were tested. As expected, the native hormone (1,25 (OH)$_2$D$_3$) increased serum calcium levels at the dosages tested (FIG. 4). FIG. 4 also shows that 2EG-S has significantly more activity in mobilizing calcium from bone than 1,25(OH)$_2$D$_3$. Administration of 2EG-S at 780 pmol/day for 4 consecutive days resulted in significant mobilization of bone calcium. 2EG-S is at least 10 times more potent than the native hormone in releasing bone calcium stores.

Intestinal calcium transport was evaluated in the same groups of animals using the everted gut sac method (FIG. 5). These results show that the compound 2EG-S has very significant activity in promoting intestinal calcium transport activity when administered at the recommended lower dosages, as compared to 1,25(OH)$_2$D$_3$. Thus, it may be concluded that 2EG-S has relatively high intestinal calcium transport activity at the tested doses.

These results further illustrate that 2EG-S is an excellent candidate for numerous human therapies as described herein. 2EG-S is an excellent candidate for treating a cancer because: (1) it has significant VDR binding, transcription activity and cellular differentiation activity; and (2) it is easily synthesized. This analog may also serve as an important therapy for bone diseases like senile osteoporosis, postmenopausal osteoporosis, steroid-induced osteoporosis, low bone turnover osteoporosis, osteomalacia, and renal osteodystrophy.

Biological Activity of (5E)-(20S)-1α,25-Dihydroxy-2-Methylene-Vitamin D$_3$ (T-2EG-S)

Figure 6:
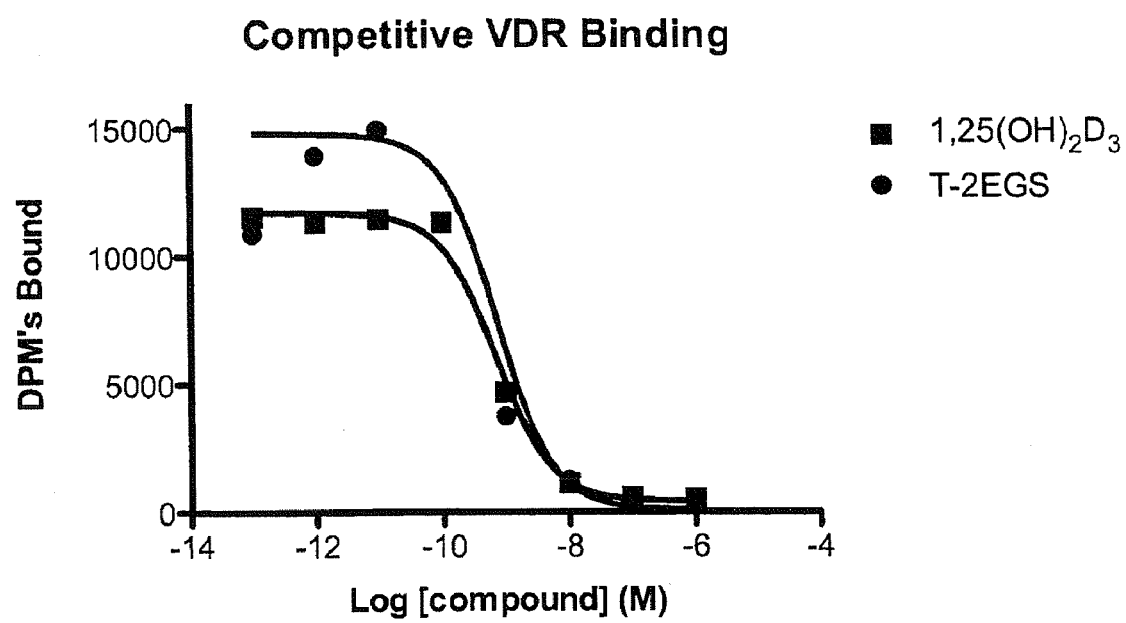
FIGS. 6-10 illustrate various biological activities of (5E)-(20S)-1α,25-dihydroxy-2-methylene-vitamin D₃, hereinafter referred to as "T-2EG-S," as compared to the native hormone 1α,25-dihydroxyvitamin D₃, hereinafter "1,25(OH)₂D₃."

The introduction of a methylene group to the 2-position, the removal of the methylene substituent at carbon 10, the introduction of a methylene substituent at carbon 4, and orienting the methyl group at carbon 20 in its epi or S configuration had little or no effect on binding to the full length recombinant rat vitamin D receptor, as compared to 1α,25-dihydroxyvitamin D$_3$. The compound T-2EG-S bound with about the same affinity to the receptor as compared to the standard 1,25-(OH)$_2$D$_3$ (FIG. 6). It might be expected from these results that compound T-2EG-S would have equivalent biological activity. Surprisingly, however, compound T-2EG-S is a highly selective analog with unique biological activity.

Figure 10:
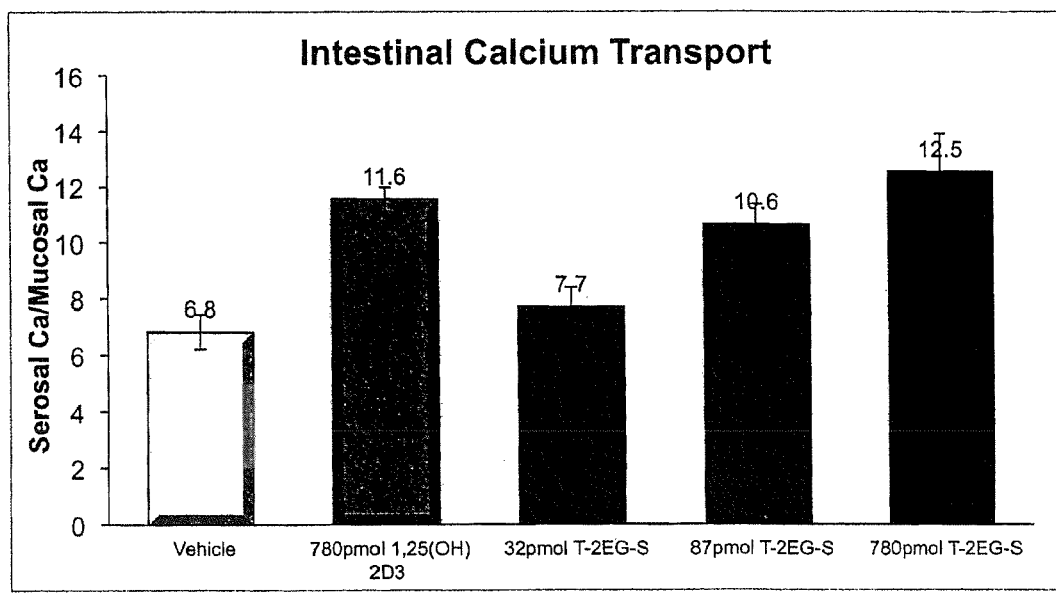

FIG. 10 shows that T-2EG-S has relatively high activity as compared to that of 1,25-dihydroxyvitamin D$_3$ (1,25(OH)$_2$ D$_3$), the natural hormone, in stimulating intestinal calcium transport. T-2EG-S has about the same potency as 1,25(OH)$_2$ D$_3$ in promoting active calcium transport across the gut.

Figure 9:
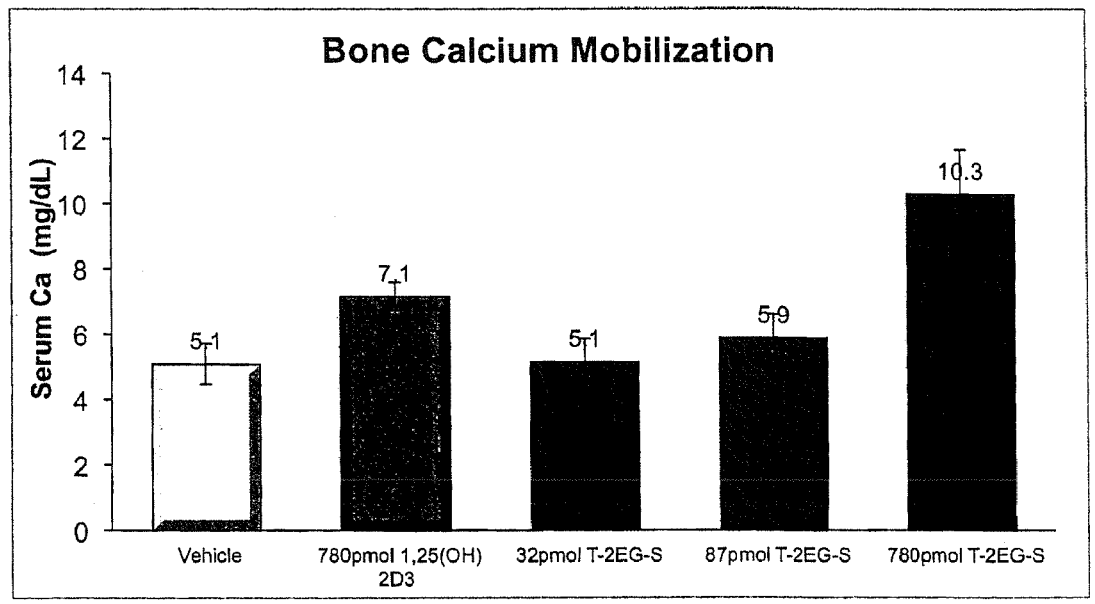

FIG. 9 demonstrates that T-2EG-S has relatively high bone calcium mobilization activity, as compared to 1,25(OH)$_2$D$_3$. T-2EG-S is more potent than the native hormone in releasing bone calcium stores.

FIGS. 9-10 thus illustrate that T-2EG-S may be characterized as having relatively high calcemic activity.

Figure 7:
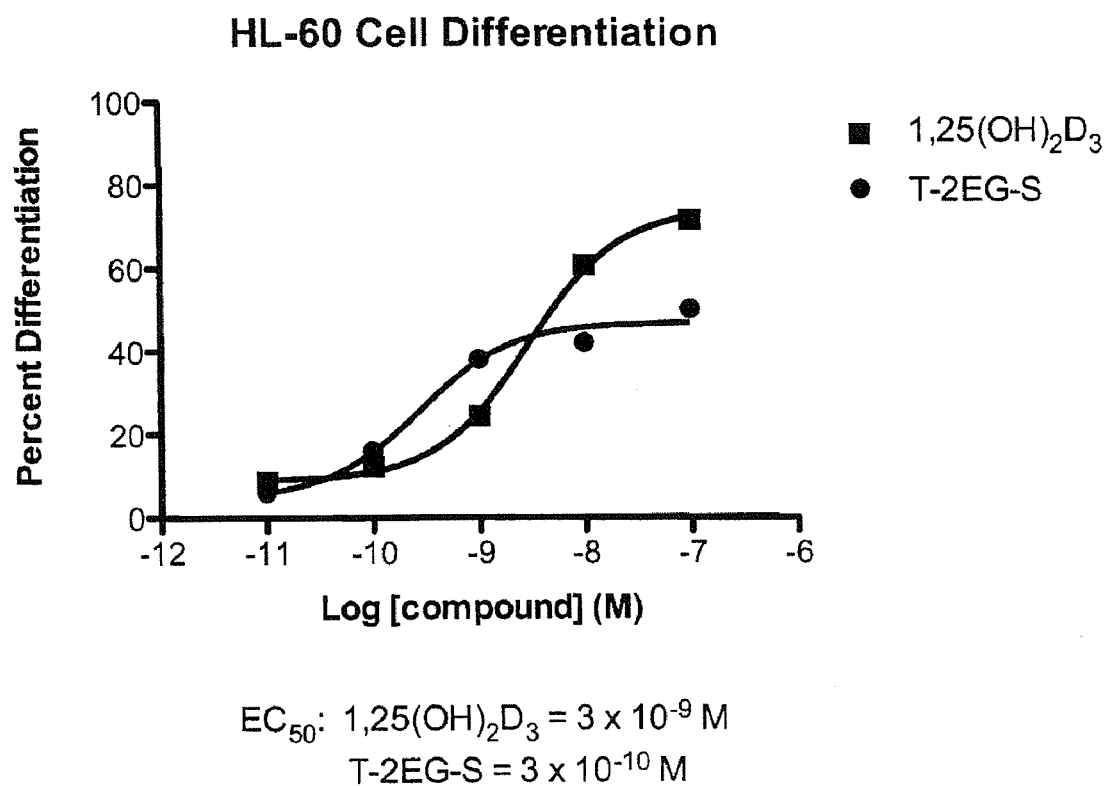

FIG. 7 illustrates that T-2EG-S is more potent than 1,25 (OH)$_2$D$_3$ on HL-60 cell differentiation, making it an excellent candidate for the treatment of a cancer, especially for the prevention or treatment of osteosarcoma, leukemia, colon cancer, breast cancer, skin cancer and prostate cancer.

Figure 8:
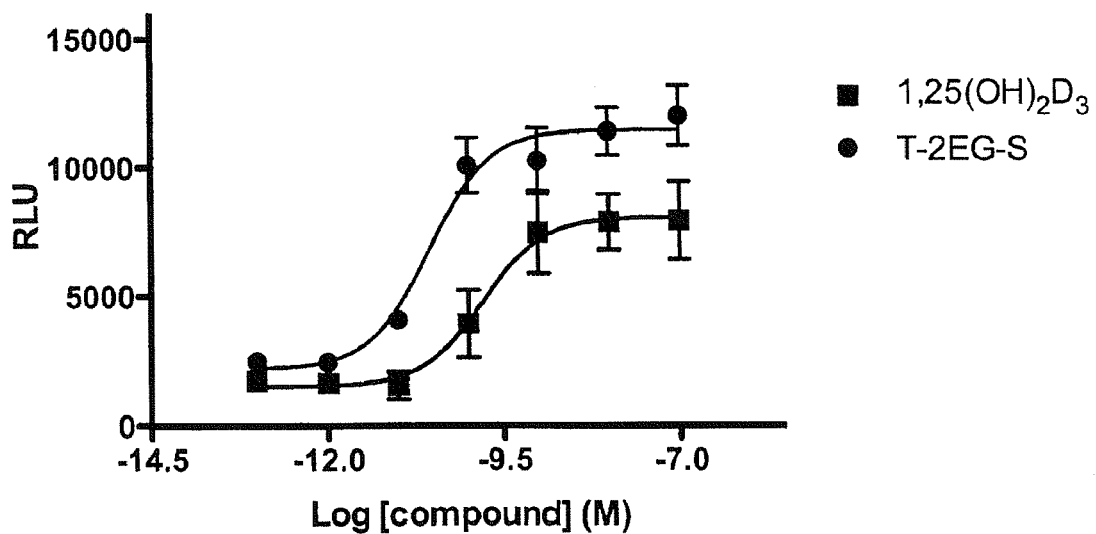

FIG. 8 illustrates that the compound T-2EG-S has greater transcriptional activity than 1α,25-dihydroxyvitamin D$_3$ in bone cells. In bone cells, T-2EG-S is about 10 times more potent than 1,25(OH)$_2$D$_3$ in increasing transcription of the 24-hydroxylase gene. This result, together with the cell differentiation activity of FIG. 7, suggests that T-2EG-S will be very effective in treating the above referred to cancers because it has direct cellular activity in causing cell differentiation, gene transcription, and in suppressing cell growth.

Interpretation of Data

VDR Binding, HL60 Cell Differentiation, and Transcription Activity.

T-2EG-S ($K_i=1\times10^{-10}$ M) has about the same activity as the natural hormone 1α,25-dihydroxyvitamin D3 ($K_i=1\times10^{-10}$M) in its ability to compete with [$^3$H]-1,25(OH)$_2$D$_3$ for binding to the full-length recombinant rat vitamin D receptor (FIG. 6). T-2EG-S is also more potent ($EC_{50}=3\times10^{-10}$ M) in its ability (efficacy or potency) to promote HL60 differentiation as compared to 1α,25-dihydroxyvitamin D$_3$ ($EC_{50}=3\times10^{-9}$ M) (See FIG. 7). Also, compound T-2EG-S ($EC_{50}=3\times10^{11}$M) has about 10 times more transcriptional activity in bone cells than 1α,25-dihydroxyvitamin D3 ($EC_{50}=2\times10^{-10}$ M) (See FIG. 8). These data indicate that T-2EG-S will have significant activity as an anti-cancer agent, especially preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D Deficient Animals.

Using vitamin D-deficient rats on a low calcium diet (0.02%), the activities of T-2EG-S and 1,25(OH)$_2$D$_3$ in intestine and bone were tested. As expected, the native hormone (1,25(OH)$_2$D$_3$) increased serum calcium levels at the dosages tested (FIG. 9). FIG. 9 also shows that T-2EG-S has significantly more activity in mobilizing calcium from bone than 1,25(OH)$_2$D$_3$. Administration of T-2EG-S at 780 pmol/day for 4 consecutive days resulted in significant mobilization of bone calcium. T-2EG-S is at least 10 times more potent than the native hormone in releasing bone calcium stores.

Intestinal calcium transport was evaluated in the same groups of animals using the everted gut sac method (FIG. 10). These results show that the compound T-2EG-S has very significant activity in promoting intestinal calcium transport activity when administered at the recommended lower dosages, as compared to 1,25(OH)$_2$D$_3$. Thus, it may be concluded that T-2EG-S has relatively high intestinal calcium transport activity at the tested doses.

These results further illustrate that T-2EG-S is an excellent candidate for numerous human therapies as described herein. T-2EG-S is an excellent candidate for treating a cancer because: (1) it has significant VDR binding, transcription activity and cellular differentiation activity; and (2) it is easily synthesized. This analog may also serve as an important therapy for bone diseases like senile osteoporosis, postmenopausal osteoporosis, steroid-induced osteoporosis, low bone turnover osteoporosis, osteomalacia, and renal osteodystrophy.

Biological Activity of
(20R)-1α,25-Dihydroxy-2-Methylene-Vitamin D$_3$
(2EG-R)

The introduction of a methylene group to the 2-position, retaining the methylene substituent at carbon 10, and orienting the methyl group at carbon 20 in its natural or R configuration had little or no effect on binding to the full length recombinant rat vitamin D receptor, as compared to 1α,25-dihydroxyvitamin D$_3$. The compound 2EG-R bound with about the same affinity to the receptor as compared to the standard 1,25-(OH)$_2$D$_3$ (FIG. 1). It might be expected from these results that compound 2EG-R would have equivalent biological activity. Surprisingly, however, compound 2EG-R is a highly selective analog with unique biological activity.

Figure 15:
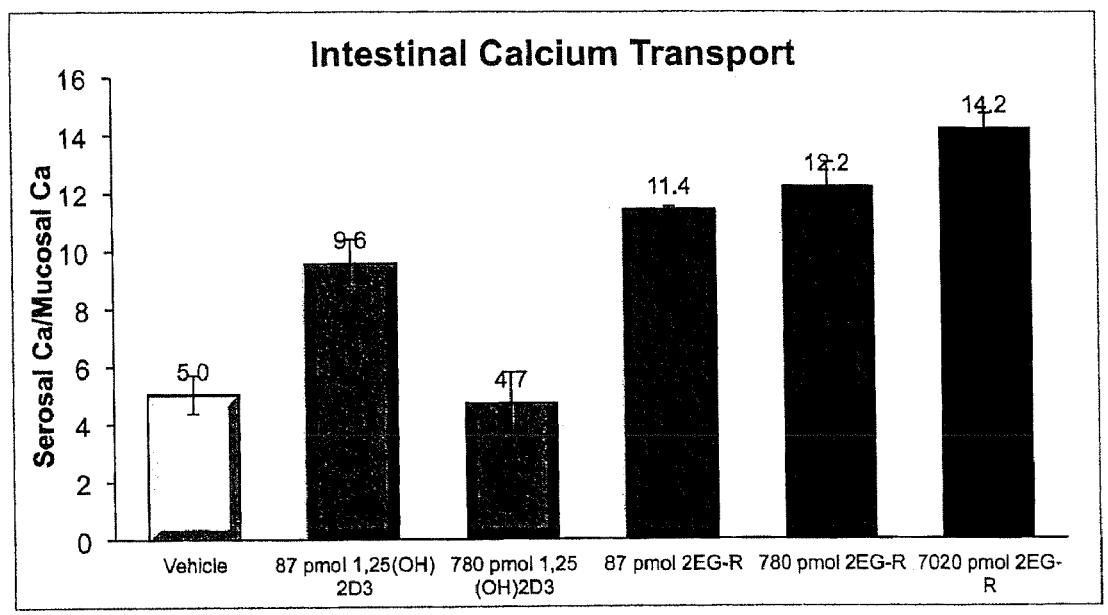

FIG. 15 shows that 2EG-R has relatively high activity as compared to that of 1,25-dihydroxyvitamin D$_3$ (1,25(OH)$_2$D$_3$), the natural hormone, in stimulating intestinal calcium transport. 2EG-R is more potent than 1,25(OH)$_2$D$_3$ in promoting active calcium transport across the gut.

Figure 14:
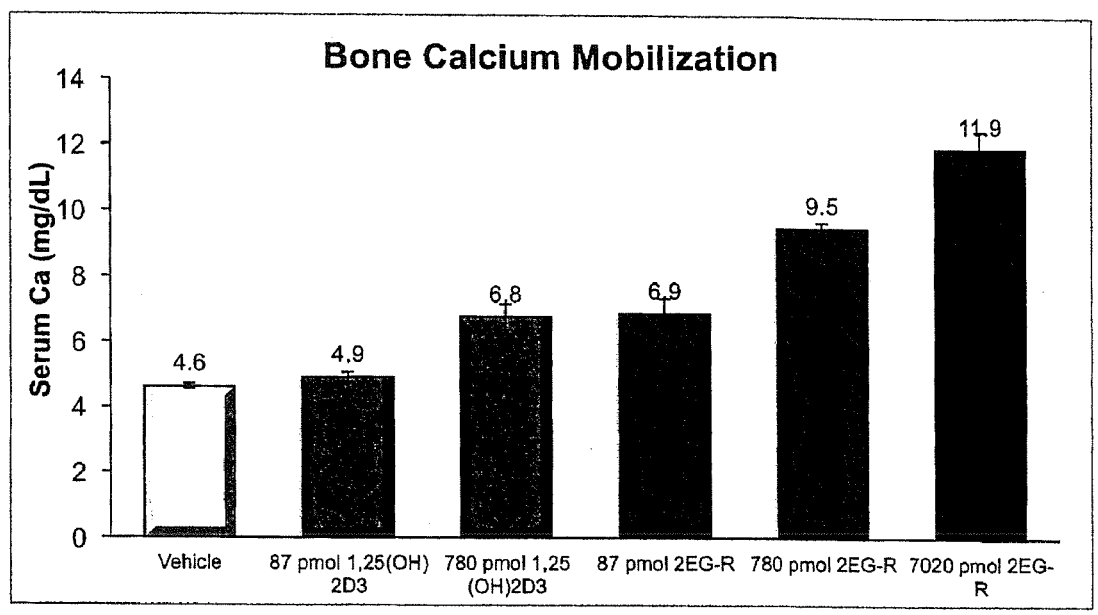

FIG. 14 demonstrates that 2EG-R has relatively high bone calcium mobilization activity, as compared to 1,25(OH)$_2$D$_3$. 2EG-R is more potent than the native hormone in releasing bone calcium stores.

FIGS. 14-15 thus illustrate that 2EG-R may be characterized as having relatively high calcemic activity.

Figure 12:
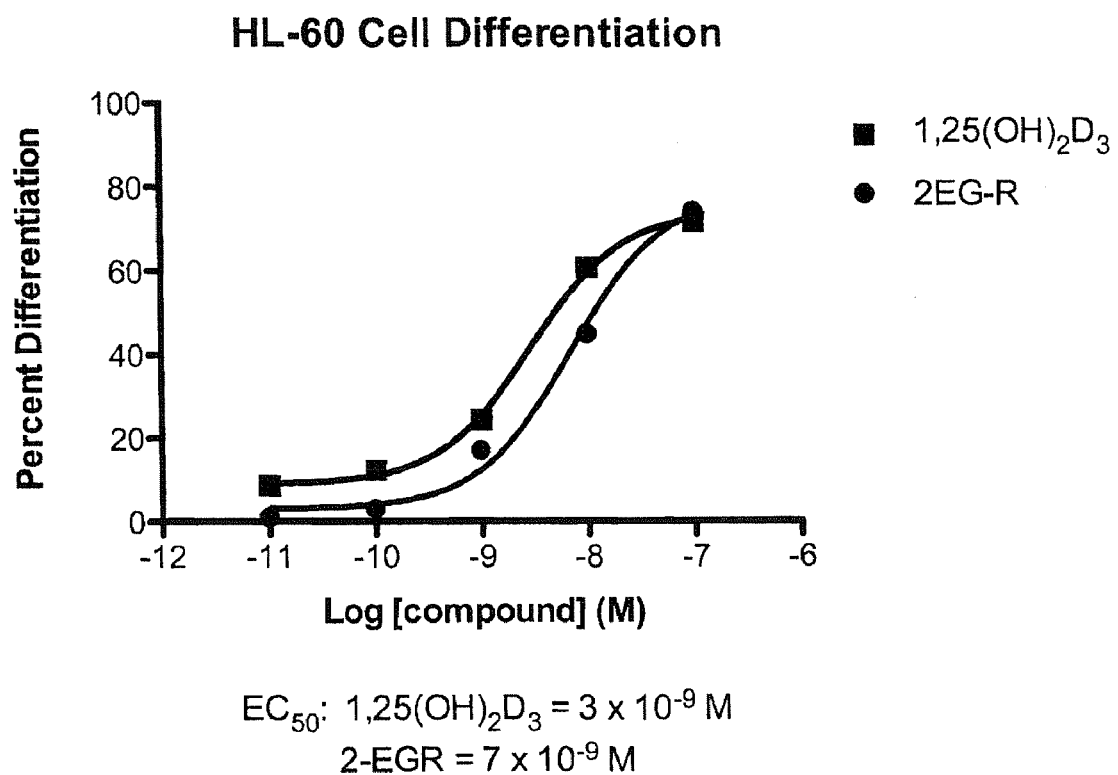

FIG. 12 illustrates that 2EG-R is more potent than 1,25(OH)$_2$D$_3$ on HL-60 cell differentiation, making it an excellent candidate for the treatment of a cancer, especially for the prevention or treatment of osteosarcoma, leukemia, colon cancer, breast cancer, skin cancer and prostate cancer.

Figure 13:
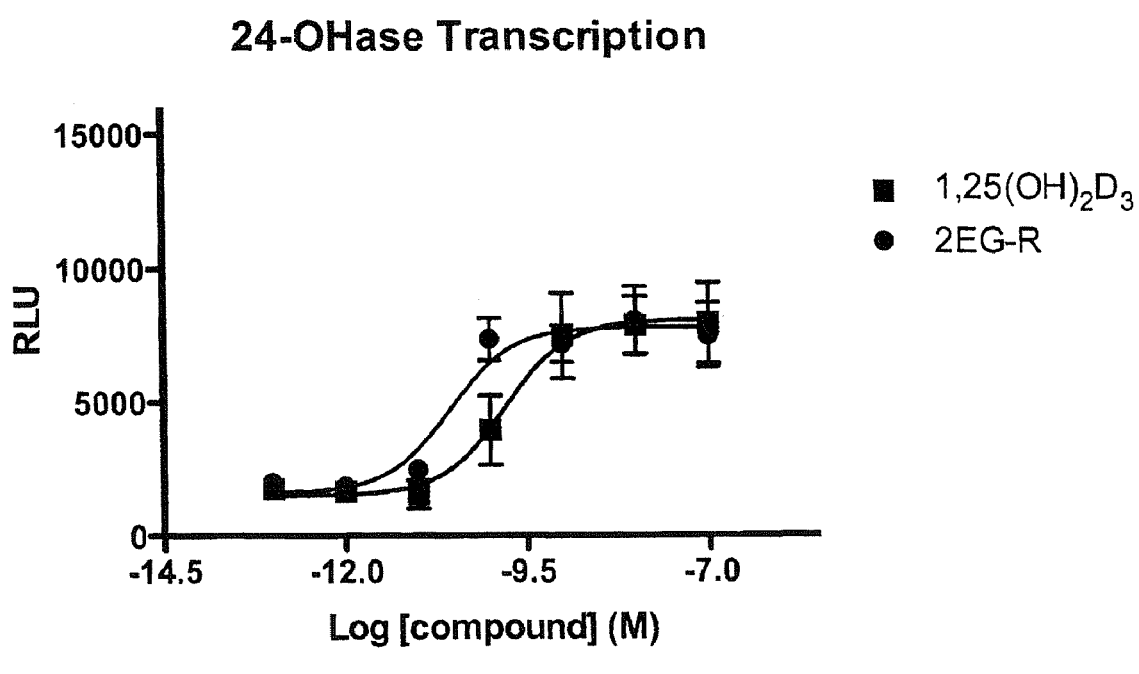

FIG. 13 illustrates that the compound 2EG-R has greater transcriptional activity than 1α,25-dihydroxyvitamin D$_3$ in bone cells. In bone cells, 2EG-R is about 10 times more potent than 1,25(OH)$_2$D$_3$ in increasing transcription of the 24-hydroxylase gene. This result, together with the cell differentiation activity of FIG. 12, suggests that 2EG-R will be very effective in treating the above referred to cancers because it has direct cellular activity in causing cell differentiation, gene transcription, and in suppressing cell growth.

Interpretation of Data

VDR Binding, HL60 Cell Differentiation, and Transcription Activity.

Figure 11:
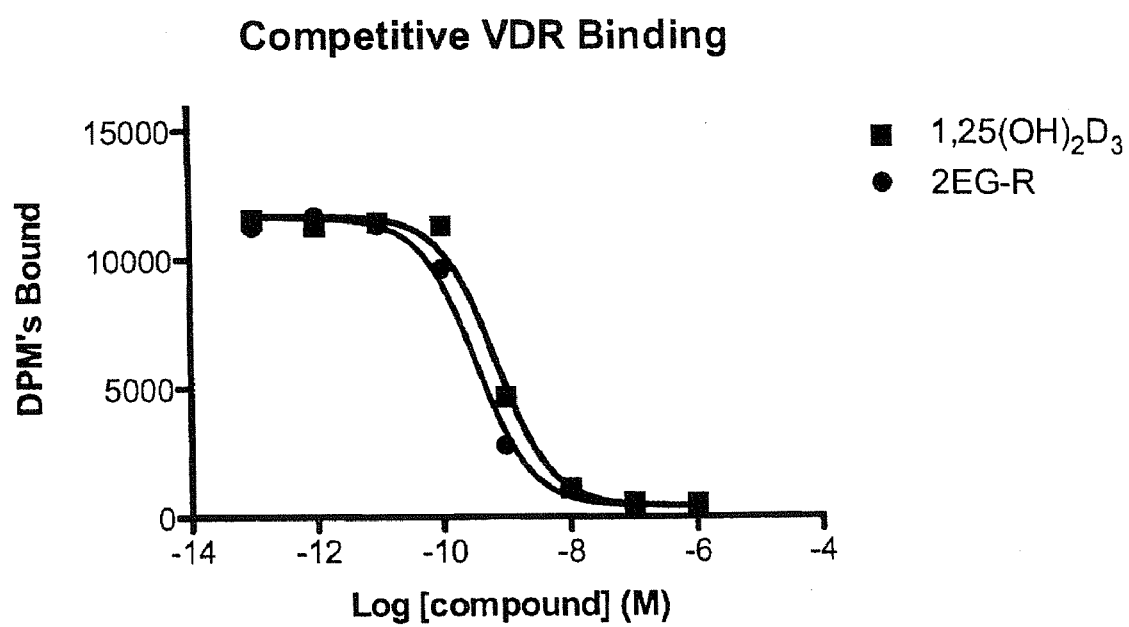
FIGS. 11-15 illustrate various biological activities of (20R)-1α,25-dihydroxy-2-methylene-vitamin $D_3$, hereinafter referred to as "2EG-R," as compared to the native hormone 1α,25-dihydroxyvitamin $D_3$, hereinafter "1,25(OH)$_2$D$_3$."

2EG-R ($K_i=6\times10^{-11}$M) has about the same activity as the natural hormone 1α,25-dihydroxyvitamin D$_3$ ($K_i=1\times10^{-10}$ M) in its ability to compete with [$^3$H]-1,25(OH)$_2$D$_3$ for binding to the full-length recombinant rat vitamin D receptor (FIG. 11). 2EG-R is slightly less potent (EC$_{50}=7\times10^{-9}$M) in its ability (efficacy or potency) to promote HL60 differentiation as compared to 1α,25-dihydroxyvitamin D$_3$ (EC$_{50}=3\times10^{-9}$ M) (See FIG. 12). Also, compound 2EG-R (EC$_{50}=3\times10^{-11}$M) has about 10 times more transcriptional activity in bone cells than 1α,25-dihydroxyvitamin D$_3$ (EC$_{50}=2\times10^{-10}$ M) (See FIG. 13). These data indicate that 2EG-R will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D-Deficient Animals.

Using vitamin D-deficient rats on a low calcium diet (0.02%), the activities of 2EG-R and 1,25(OH)$_2$D$_3$ in intestine and bone were tested. As expected, the native hormone (1,25(OH)$_2$D$_3$) increased serum calcium levels at the dosages tested (FIG. 14). FIG. 14 also shows that 2EG-R has significantly more activity in mobilizing calcium from bone than 1,25(OH)$_2$D$_3$. Administration of 2EG-R at 780 pmol/day for 4 consecutive days resulted in significant mobilization of bone calcium. 2EG-R is at least 10 times more potent than the native hormone in releasing bone calcium stores.

Intestinal calcium transport was evaluated in the same groups of animals using the everted gut sac method (FIG. 15). These results show that the compound 2EG-R has very significant activity in promoting intestinal calcium transport activity when administered at the recommended lower dosages, as compared to 1,25(OH)$_2$D$_3$. Thus, it may be concluded that 2EG-R has relatively high intestinal calcium transport activity at the tested doses.

These results further illustrate that 2EG-R is an excellent candidate for numerous human therapies as described herein. 2EG-R is an excellent candidate for treating a cancer because: (1) it has significant VDR binding, transcription activity and cellular differentiation activity; and (2) it is easily synthesized. This analog may also serve as an important therapy for bone diseases like senile osteoporosis, postmenopausal osteoporosis, steroid-induced osteoporosis, low bone turnover osteoporosis, osteomalacia, and renal osteodystrophy.

For prevention and/or treatment purposes, the compounds of this invention defined by formula I, Ia, Ib, and Ic may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 2EG-S of formula Ia, and T-2EG-S of formula Ib, and 2EG-R of formula Ic may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly 2EG-S, T-2EG-S, and 2EG-R, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly 2EG-S, T-2EG-S, and 2EG-R, as defined by the above formula I, Ia, Ib, and Ic as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, particularly 2EG-S, T-2EG-S, and 2EG-R, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 2EG-S, T-2EG-S, and 2EG-R, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:
1. A compound having the formula:

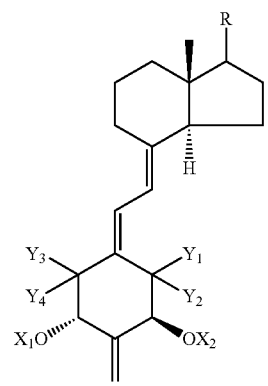

where $X_1$ and $X_2$ are selected from the group consisting of hydrogen and a hydroxy-protecting group, where $Y_1$ and $Y_2$ are each hydrogen or taken together represent a methylene group, where $Y_3$ and $Y_4$ are each hydrogen or taken together represent a methylene group, with the provisos that when $Y_1$ and $Y_2$ are both hydrogen then $Y_3$ and $Y_4$ must be a methylene group, or when $Y_1$ and $Y_2$ taken together are a methylene group then $Y_3$ and $Y_4$ must both be hydrogen, or when $Y_3$ and $Y_4$ are both hydrogen then $Y_1$ and $Y_2$ must be a methylene group, or when $Y_3$ and $Y_4$ taken together are a methylene group then $Y_1$ and $Y_2$ must both be hydrogen, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

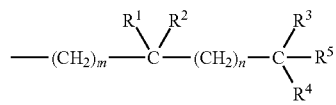

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —$(CH_2)_m$—, —$CR_1R_2$— or —$(CH_2)_n$— at positions 20, 22, and 23, respectively, may be replaced by an oxygen or sulfur atom.

2. The compound of claim 1 wherein $X_1$ and $X_2$ are both hydrogen.

3. The compound of claim 1 wherein R is selected from:

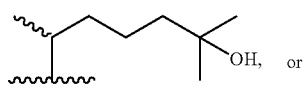

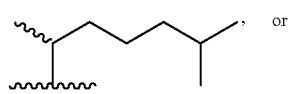

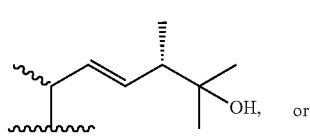

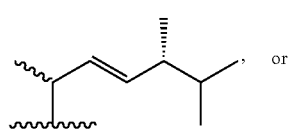

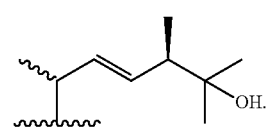

4. The compound of claim 3 wherein $X_1$ and $X_2$ are both hydrogen.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 μg to about 1000 μg per gram of composition.

7. The pharmaceutical composition of claim 5 wherein said effective amount comprises from about 0.1 μg to about 500 μg per gram of composition.

8. A compound having the formula:

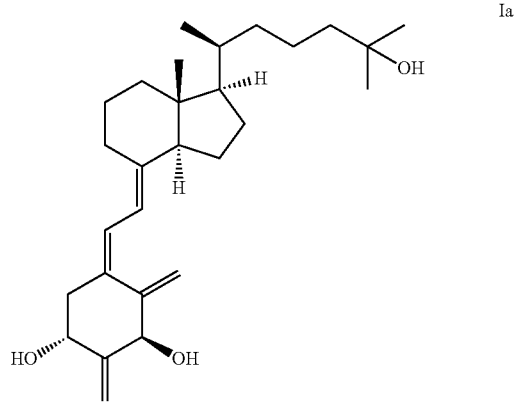 [SMILES: C=C1/C(=C\C=C2/CCC[C@]3(C)[C@@H]([C@@H](C)CCCC(C)(C)O)CC[C@@H]23)C[C@@H](O)C(=C)[C@@H]1O]

and named (20S)-1α,25-dihydroxy-2-methylene-vitamin $D_3$.

9. A pharmaceutical composition containing an effective amount of (20S)-1α,25-dihydroxy-2-methylene-vitamin $D_3$ together with a pharmaceutically acceptable excipient.

10. The pharmaceutical composition of claim 9 wherein said effective amount comprises from about 0.01 μg to about 1000 g per gram of composition.

11. The pharmaceutical composition of claim 9 wherein said effective amount comprise from about 0.1 μg to about 500 μg per gram of composition.

12. A compound having the formula:

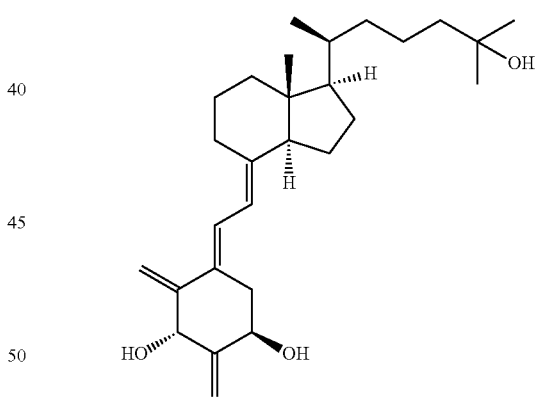

and named (5E)-(20S)-1α,25-dihydroxy-2-methylene-vitamin $D_3$.

13. A pharmaceutical composition containing an effective amount of (5E)-(20S)-1α,25-dihydroxy-2-methylene-vitamin $D_3$ together with a pharmaceutically acceptable excipient.

14. The pharmaceutical composition of claim 13 wherein said effective amount comprises from about 0.01 μg to about 1000 μg per gram of composition.

15. The pharmaceutical composition of claim 13 wherein said effective amount comprises from about 0.1 μg to about 500 μg per gram of composition.

16. A compound having the formula:

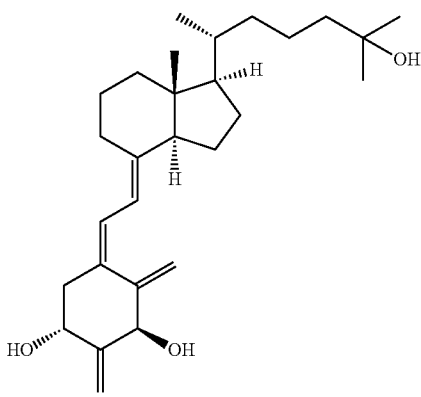 [SMILES: C=C1/C(=C\C=C2/CCC[C@]3(C)[C@@H]([C@H](C)CCCC(C)(C)O)CC[C@@H]23)C[C@@H](O)C(=C)[C@@H]1O]

and named (20R)-1α,25-dihydroxy-2-methylene-vitamin D₃.

17. A pharmaceutical composition containing an effective amount of (20R)-1α,25-dihydroxy-2-methylene-vitamin D₃ together with a pharmaceutically acceptable excipient.

18. The pharmaceutical composition of claim 17 wherein said effective amount comprises from about 0.01 μg to about 1000 μg per gram of composition.

19. The pharmaceutical composition of claim 17 wherein said effective amount comprises from about 0.01 μg to about 500 μg per gram of composition.

20. A method of treating a disease selected from the group consisting of osteosarcoma, leukemia, colon cancer, breast cancer, skin cancer or prostate cancer comprising administering to a subject with said disease an effective amount of a 2-methylene-vitamin D analog having the formula:

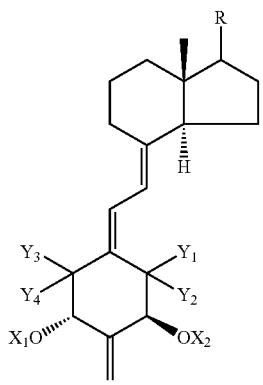

where $X_1$ and $X_2$ are selected from the group consisting of hydrogen and a hydroxy-protecting group, where $Y_1$ and $Y_2$ are each hydrogen or taken together represent a methylene group, where $Y_3$ and $Y_4$ are each hydrogen or taken together represent a methylene group, with the provisos that when $Y_1$ and $Y_2$ are both hydrogen then $Y_3$ and $Y_4$ must be a methylene group, or when $Y_1$ and $Y_2$ taken together are a methylene group then $Y_3$ and $Y_4$ must both be hydrogen, or when $Y_3$ and $Y_4$ are both hydrogen then $Y_1$ and $Y_2$ must be a methylene group, or when $Y_3$ and $Y_4$ taken together are a methylene group then $Y_1$ and $Y_2$ must both be hydrogen, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH₂OY, —C≡CY and —CH═CHY, where the double bond in the side chain may have the cis or trans geometry, and where Y is selected from hydrogen, methyl, —COR³ and a radical of the structure:

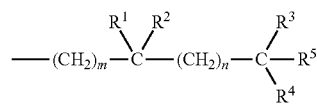

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =CR²R³, or the group —(CH₂)$_p$—, where p is an integer from 2 to 5, and where $R^3$ and $R^4$, taken together, represent an oxo group, or the group —(CH₂)$_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)$_m$—, —CR₁R₂— or —(CH₂)$_n$— at positions 20, 22, and 23, respectively, may be replaced by an oxygen or sulfur atom.

21. The method of claim 20 wherein the vitamin D analog is administered orally.

22. The method of claim 20 wherein the vitamin D analog is administered parenterally.

23. The method of claim 20 wherein the vitamin D analog is administered transdermally.

24. The method of claim 20 wherein the vitamin D analog is administered rectally.

25. The method of claim 20 wherein the vitamin D analog is administered nasally.

26. The method of claim 20 wherein the vitamin D analog is administered sublingually.

27. The method of claim 20 wherein the vitamin D analog is administered in a dosage of from about 0.01 μg/day to about 1000 μg/day.

28. The method of claim 20 wherein the vitamin D analog has the formula:

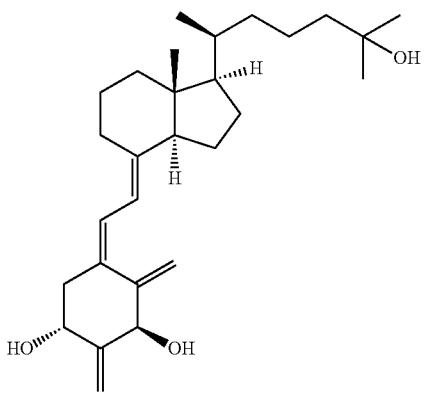

and is named (20S)-1α,25-dihydroxy-2-methylene-vitamin D₃.

29. The method of claim 20 wherein the vitamin D analog has the formula:

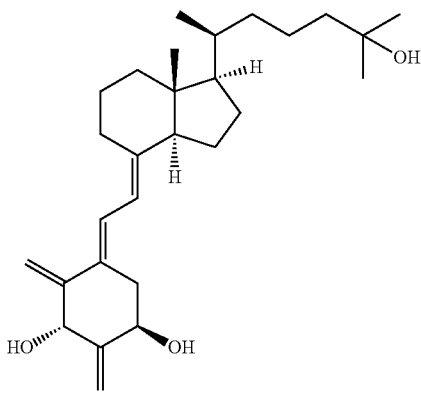 [SMILES: C=C1/C(=C/C=C2\CCC[C@]3(C)[C@@H]([C@@H](C)CCCC(C)(C)O)CC[C@@H]23)C[C@@H](O)C(=C)[C@@H]1O]

and is named (5E)-(20S)-1α,25-dihydroxy-2-methylene-vitamin D₃.

30. The method of claim 20 wherein the vitamin D analog has the formula:

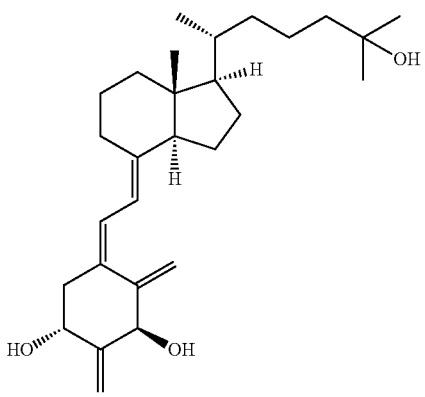 [SMILES: C=C1/C(=C\C=C2/CCC[C@]3(C)[C@@H]([C@H](C)CCCC(C)(C)O)CC[C@@H]23)C[C@@H](O)C(=C)[C@@H]1O]

and is named (20R)-1α,25-dihydroxy-2-methylene-vitamin D₃.

31. A method of treating metabolic bone disease where it is desired to maintain or increase bone mass comprising administering to a patient with said disease an effective amount of a compound having the formula:

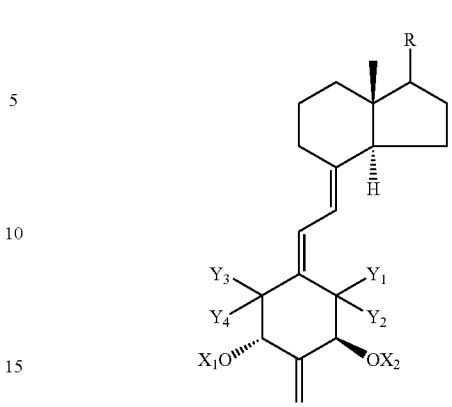

where $X_1$ and $X_2$ are selected from the group consisting of hydrogen and a hydroxy-protecting group, where $Y_1$ and $Y_2$ are each hydrogen or taken together represent a methylene group, where $Y_3$ and $Y_4$ are each hydrogen or taken together represent a methylene group, with the provisos that when $Y_1$ and $Y_2$ are both hydrogen then $Y_3$ and $Y_4$ must be a methylene group, or when $Y_1$ and $Y_2$ taken together are a methylene group then $Y_3$ and $Y_4$ must both be hydrogen, or when $Y_3$ and $Y_4$ are both hydrogen then $Y_1$ and $Y_2$ must be a methylene group, or when $Y_3$ and $Y_4$ taken together are a methylene group then $Y_1$ and $Y_2$ must both be hydrogen, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH₂OY, —C≡CY and —CH═CHY, where the double bond in the side chain may have the cis or trans geometry, and where Y is selected from hydrogen, methyl, —COR⁵ and a radical of the structure:

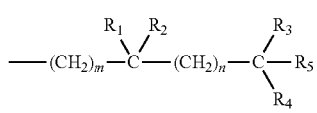

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group ═CR²R³, or the group —(CH₂)ₚ—, where p is an integer from 2 to 5 and where $R^3$ and $R^4$, taken together, represent an oxo group. Or the group —(CH₂)_q—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 where the disease is senile osteoporosis.

40. The method of claim 31 where the disease is postmenopausal osteoporosis.

41. The method of claim 31 where the disease is steroid-induced osteoporosis.

42. The method of claim 31 where the disease is low bone turnover osteoporosis.

43. The method of claim 31 where the disease is osteomalacia.

44. The method of claim 31 where the disease is renal osteodystrophy.

45. The method of claim 31 wherein the compound has the formula:

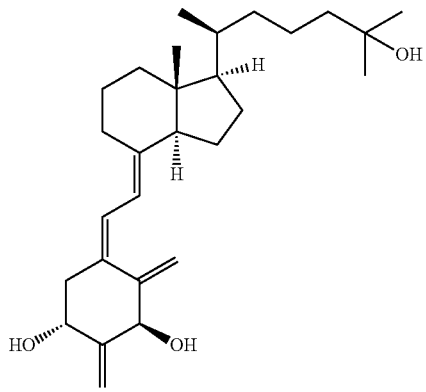 [SMILES: C=C1/C(=C\C=C2/CCC[C@]3(C)[C@@H]([C@@H](C)CCCC(C)(C)O)CC[C@@H]23)C[C@@H](O)C(=C)[C@@H]1O]

and is named (20S)-1α,25-dihydroxy-2-methylene-vitamin D$_3$.

46. The method of claim 31 wherein the compound has the formula:

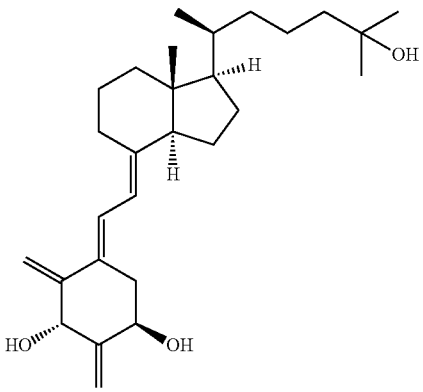 [SMILES: C=C1/C(=C/C=C2\CCC[C@]3(C)[C@@H]([C@@H](C)CCCC(C)(C)O)CC[C@@H]23)C[C@@H](O)C(=C)[C@@H]1O]

and is named (5E)-(20S)-1α,25-dihydroxy-2-methylene-vitamin D$_3$.

47. The method of claim 31 wherein the compound has the formula:

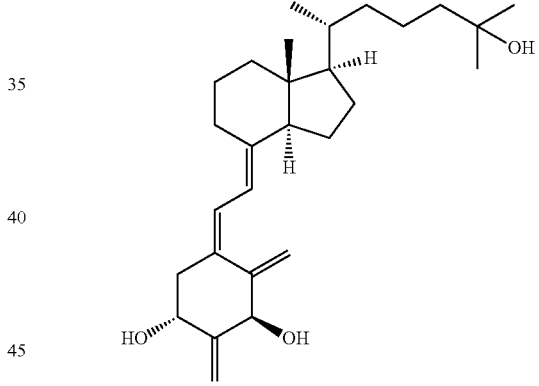

and is named (20R)-1α,25-dihydroxy-2-methylene-vitamin D$_3$.

* * * * *